US010753946B2

(12) United States Patent
Mattsson et al.

(10) Patent No.: US 10,753,946 B2
(45) Date of Patent: Aug. 25, 2020

(54) ALLERGEN

(71) Applicant: PHADIA AB, Uppsala (SE)

(72) Inventors: Lars Mattsson, Uppsala (SE); Ulrica Olsson, Uppsala (SE); Thomas Lundgren, Uppsala (SE); Jonas Lidholm, Knivsta (SE); Håkan Larsson, Bälinge (SE)

(73) Assignee: PHADIA AB, Uppsala (SE)

( * ) Notice: Subject to any disclaimer, the term of this patent is extended or adjusted under 35 U.S.C. 154(b) by 642 days.

(21) Appl. No.: 15/327,253

(22) PCT Filed: Jul. 20, 2015

(86) PCT No.: PCT/SE2015/050828
§ 371 (c)(1),
(2) Date: Jan. 18, 2017

(87) PCT Pub. No.: WO2016/013971
PCT Pub. Date: Jan. 28, 2016

(65) Prior Publication Data
US 2017/0219602 A1 Aug. 3, 2017

(30) Foreign Application Priority Data

Jul. 21, 2014 (SE) .................................... 1450907

(51) Int. Cl.
G01N 33/68 (2006.01)
C07K 14/47 (2006.01)
A61K 39/35 (2006.01)
A61P 37/08 (2006.01)

(52) U.S. Cl.
CPC ......... G01N 33/6854 (2013.01); A61K 39/35 (2013.01); A61P 37/08 (2018.01); C07K 14/47 (2013.01)

(58) Field of Classification Search
None
See application file for complete search history.

(56) References Cited

U.S. PATENT DOCUMENTS

| 6,019,972 | A * | 2/2000 | Gefter | C07K 14/415 424/185.1 |
| 9,164,101 | B2 | 10/2015 | Mattsson et al. | |
| 2005/0101031 | A1 | 5/2005 | Hiller et al. | |
| 2013/0045233 | A1 * | 2/2013 | Mattsson | A61K 39/35 424/276.1 |

FOREIGN PATENT DOCUMENTS

WO 2011133105 A1 10/2011

OTHER PUBLICATIONS

Wade et al. 'Genome Sequence, Comparative Analysis, and Population Genetics of the Domestic Horse.' Science. 326(5954):865-867, 2009.*
Lerner et al. 'Tapping the immunological repertoire to produce antibodies of predetermined specificity.' Nature. 299:592-596, 1982.*
https://www.uniprot.org/uniparc/UPI000155EE49 (Jun. 26, 2007).
https://www.uniprot.org/uniparc/UPI0001FB0512 (Feb. 2, 2001).
Official Action dated Jul. 31, 2018 from corresponding European Application No. 15750835.9.
Official Action dated May 28, 2019 from corresponding Japanese Application No. 2017-503551 with English Translation.
Wade, CM et al., Genome sequence, comparative analysis and population genetics of the domestic horse (Equus caballus), Science, vol. 326, No. 5954, pp. 865-867 (Nov. 6, 2009).
Uniprot F6UF44-HORSE, Jul. 27, 2011.
Toit et al., Randomized Trial of Peanut Consumption in Infants at Risk for Peanut Allergy, The New England Journal of Medicine, vol. 372, No. 9, p. 803-813 (Feb. 26, 2015).
Ebisawa et al., Clinical Utility of IgE Antibodies to w-5 Gliadin in the Diagnosis of Wheat Allergy: A Pediatric Multicenter Challenge Study, Int Arch Allergy Immunol, 158:71-76 (online Dec. 29, 2011).
Ebisawa et al., Measurement of Ara h 1-, 2-, and 3-specific IgE antibodies is useful in diagnosis of peanut allergy in Japanese children, Pediatric Allergy Immunol, 23:573-581 (May 15, 2012).
Botros et al., Biochemical characterization and surfactant properties of horse allergen, Eur. J. Biochem, 268:3126-3136 (Apr. 5, 2001).
Botros et al., Cross-antigenicity of horse serum albumin with dog and cat albumins: study of three short peptides with significant inhibitory activity towards specific human IgE and IgE antibodies, Immunology, 88:340-347 (Mar. 11, 1996).
Akdis et al., Allergy and hypersensitivity Mechanisms of allergic disease, Current Opinion in Immunology, 18:718-726 (Sep. 16, 2006).
Akdis et al., Mechanisms of allegen-specific immunotherapy, J Allergy Clin Immunology, 119:780-9 (published online Mar. 6, 2007).
Asarnoj et al., IgE to peanut allegen components: relation to peanut symptoms and pollen sensitization in 8-year-olds, Allergy, 65:1189-1195 (Dec. 28, 2009).
Asarnoj et al., Peanut component Ara h 8 sensitization and tolerance to peanut, J Allergy Clin Immunol 130:468-72 (published online Jun. 26, 2012).
Breiteneder et al., Recombinant Allergens; Basic and Practical Considerations, 8th International Paul Ehrlich Seminar, p. 1-7 (1997).
Cabanas et al., Importance of albumin in cross-reactivity among cat, dog and horse allergens, Invest Allergol Clin Immunol, vol. 10(2):71-77 (Mar.-Apr. 2000).

(Continued)

Primary Examiner — Nora M Rooney
(74) Attorney, Agent, or Firm — Porter Wright Morris & Arthur LLP

(57) ABSTRACT

The invention relates to a novel horse allergen consisting of a heterodimeric protein having a first peptide chain and a second peptide chain together having an overall sequence identity of at least 70% with the combined sequences of SEQ ID NO:3 and SEQ ID NO: 4, as well as a single chain protein having an overall sequence identity of at least 70%, such as 75%, 80%, 85%, 90%, 95%, or 98%, with the combined amino acid sequences according to SEQ ID NO: 3 and SEQ ID NO: 4. The invention further relates to the use of the protein in methods of diagnosis and therapy of Type I allergy, and kits and compositions for use in such methods.

Figure 1:
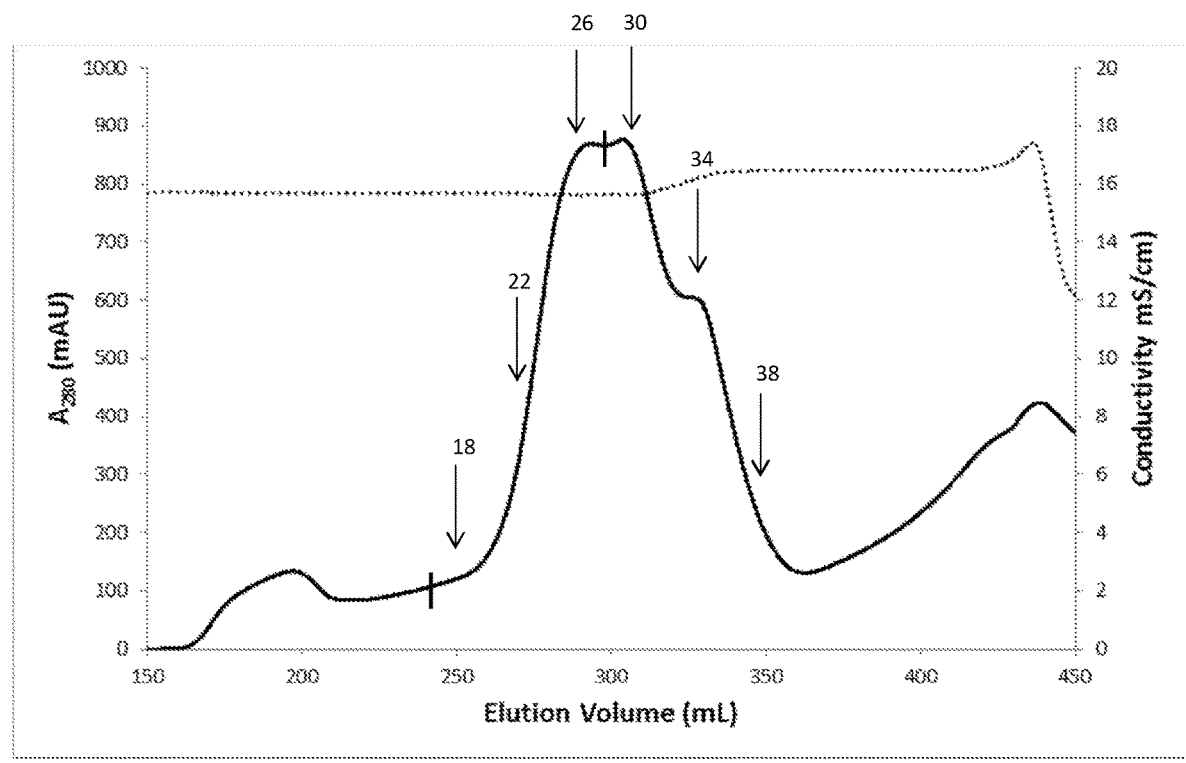

14 Claims, 14 Drawing Sheets
Specification includes a Sequence Listing.

(56) References Cited

OTHER PUBLICATIONS

Canonica et al., A WAO-ARIA-GA2LEN consensus document on molecular-based allergy diagnostics, World Allergy Organization Journal, 6:17, pp. 1-39 (Oct. 3, 2013).
Caubet, MD et al., Significance of ovomucoid- and ovalbumin-specific IgE/IgG4 ratios in egg allergy, J Allergy Clin Immunol, 129:739-47 (online Jan. 24, 2012).
F. Codreanu et al., A Novel Immunoassay Using Recombinant Allergens Simplifies Peanut Allergy Diagnosis, Int Arch Allergy Immunol, 154:216-226 (online Sep. 21, 2010).
Cromwell, PhD et al., Strategies for Recombinant Allergen Vaccines and Fruitful Results from First Clinical Studies, Immunol Allergy Clin N Am, 26:261-281 (2006).
Custovic, MD, PhD et al., Allergen-specific IgG antibody levels modify the relationship between allergen-specific IgE and wheezing in childhood, J Allergy Clin Immunol, 127:1480-5 (online Apr. 13, 2011).
Dandeu et al., Hydrophobic interaction chromatography for isolation and purification of Equ.c1, the horse major allergen, Journal of Chromatography, 621:23-31 (Aug. 6, 1993).
Jutel, MD et al., Allergen-specific immunotherapy with recombinant grass pollen allergens, J Allergy Clin Immunol, 116:608-13 (online Aug. 1, 2005).
Kim et al, Current asthma and respiratory symptoms among pupils in relation to dietary factors and allergens in the school environment, Indoor Air, 15:170-182 (Feb. 18, 2005).
Laukaitis et. al., Evolution of the secretoglobins: a genomic and proteomic view, Biological Journal of the Linnean Society, 84:493-501 (Oct. 7, 2004).
Liccardi et al., Sensitization to Horse Allergens in Italy: A Multicentre Study in Urban Atopic Subjects without Occupational Exposure, Int Arch Allergy Immunol, 155:412-417 (online Feb. 22, 2011).
Dewitt et al., Molecular and immunological characterization of a novel timothy grass (*Phleum pratense*) pollen allergen, Phl p. 11, Clin Exp Allergy, 32:1329-1340 (Apr. 25, 2002).
Masthoff et al., Sensitization to Cor a 9 and Cor a 14 is highly specific for a hazelnut allergy with objective symptoms in Dutch children and adults, J Allergy Clin Immunol, 132:393-9 (published online Apr. 10, 2013).
Matsuo et al., Sensitivity and specificity of recombinant x-5 gliadin-specific IgE measurement for the diagnosis of wheat-dependent exercise-induced anaphylaxis, Allergy, 63:233-236 (Jun. 25, 2007).
Mattsson, et al., Prostatic kallikrein: A new major dog allergen, J Allergy Clin Immunol, 123:362-8 (published online Jan. 12, 2009).
Mcdonald et al., Latherin: A Surfactant Protein of Horse Sweat and Saliva, PLoS ONE, 4(5): e5726 (May 29, 2009).
Muller et al., IgE to recombinant allergens Api m 1, Ves v 1, and Ves v 5 distinguish double sensitization from crossreaction in venom allergy, Allergy, 67:1069-1073 (Apr. 19, 2012).

Nicolaou, MD et al., Allergy or tolerance in children sensitized to peanut: Prevalence and differentiation using component-resolved diagnostics, J Allergy Clin Immunol, 125:191-7 (Oct. 9, 2009).
Perzanowski et al., Different sensitization profile for asthma, rhinitis, and eczema among 7-8-year-old children: Report from the Obstructive Lung Disease in Northern Sweden studies, Pediatr Allergy Immunol, 14:91-99 (Dec. 20, 2002).
Saarelainen et al., Animal-derived lipocalin allergens exhibit immunoglobulin E cross-reactivity, Clinical and Experimental Allergy, 38:374-381 (Oct. 16, 2007).
Saarne et al., Rational design of hypoallergens applied to the major cat allergen Fel d 1, Clin Exp Allergy, 35:657-663 (Jan. 11, 2005).
Smith et al., Fel d 4, a cat lipocalin allergen, Clin Exp Allergy, 34:1732-1738 (Jul. 27, 2004).
Spitzauer et al., Characterisation of Dog Allergens by Means of Immunoblotting, Int Arch Allergy Immunol, 100:60-67 (1993).
Stumvoll, PhD et al., Identification of cross-reactive and genuine Parietaria judaica pollen allergens, J Allergy Clin Immunol, 111:974-9 (Jan. 7, 2003).
Tutluoglu et al., Sensitization to horse hair, symptoms and lung function in grooms, Clin Exp Allergy 32:1170-1173 (Mar. 29, 2002).
Uermosi et al., IgG-mediated down-regulation of IgE bound to mast cells: a potential novel mechanism of allergen-specific desensitization, Allergy, 69:338-347 (Oct. 20, 2013).
Uermosi et al., Mechanisms of allergen-specific desensitization, J Allergy Clin Immunol, 126:375-83 (published online Jul. 12, 2010).
Wainstein et al., Combining skin prick, immediate skin application and specific-IgE testing in the diagnosis of peanut allergy in children, Pediatr Allergy Immunol, 18:231-239 (Oct. 27, 2006).
Valenta et al., The recombinant allergen-based concept of componentresolved diagnostics and immunotherapy (CRD and CRIT), Clinical and Experimental Allergy, vol. 29, pp. 896-904 (1999).
Valenta et al., Recombinant allergens for immunotherapy, J Allergy Clin Immunol, 119:826-30 (online Mar. 10, 2007).
Botros et al., Thiophilic adsorption chromatography: purification of Equ c2 and Equ c3, two horse allergens from horse sweat, Journal of Chromatography B, 710:57-65 (Mar. 5, 1998).
Gregoire et al., cDNA Cloning and Sequencing Reveal the Major Horse Allergen Equ c1 to Be a Glycoprotein Member of the Lipocalin Superfamily, vol. 271, No. 51, pp. 32951-32959 (Dec. 20, 1996).
Gronlund et al., The Major Cat Allergen, Fel d 1, in Diagnosis and Therapy, Int Arch Allergy Immunol, 151:265-274 (online 2009).
Hiller et al., Microarrayed allergen molecules: diagnostic gatekeepers for allergy treatment, The FASEB Journal, 16:414-416 (Mar. 2002).
NCBI, Accession No. XM008515074, PREDICTED: Equus przewalskii major allergen I polypeptide chain 2-like (LOC103547701), transcript variant X1, mRNA, NCBI (Jul. 14, 2014).
NCBI, Accession No. XM008515073, PREDICTED: Equus przewalskii major allergen I polypeptide chain 1-like (LOC103547699), mRNA, NCBI (Jul. 14, 2014).

* cited by examiner

Figure 6 a)
ATGAAGCGGGCTGGTGCTCTCGTGCTGCTCTGGACCACCTTGCTTCTGA
TCCCAGGCAGAAATTGTGACATTTGCCCAGCCGTGAAGGAAGATGTTAA
TATATTCCTGACAGGAACCCCTGATGACTATGTTAAAAAGTTTCACAGT
ACCAACGCAATCCTGTAATATTGGCCAATGCTGAAAAGCTAAAGAACTG
CATTGATAAGAAATTGACAGCCGAGGATAAGGAGAATGCCCTCAGTGTG
CTGGAGAAAATATACTCAAGTGATTTTTGTTAA (SEQ ID NO: 45)

b)
MKRAGALVLLWTTLLLIPGRNCDICPAVKEDVNIFLTGTPDDYVKKVSQYQ
RNPVILANAEKLKNCIDKKLTAEDKENALSVLEKIYSSDFC (SEQ ID NO: 1)

c)

```
Equus 1    DICPAVKEDVNIFLTGTPDDYVKKVSQYQRNPVILANAEKLKNCIDKKLTAEDKENALSV  60
           +ICPAVK DV++FL GTPD YV++V+QY   PV+LANA  L+NC+D K+T EDKENALSV
Felid 1    EICPAVKRDVDLFLMGTPDKYVEQVAQYNARPVVLANAPNLKNCVDAKMTEEDKENALSV  78

Equus 1    LEKIYSSDFC  70
           L+KIY+S  C
Felid 1    LDKIYTSPLC  88
```

Figure 7 a)
ATGAAGGGGGGCACTGCTTGTGCTGGCCTTGCTGGTGACCAGAGAGC
TGGGCATCAAGATGGCGGAAGCTTGCCCGAGTTTTTATGCAGTCCTT
GGTGTGTTGTCCCTTGGAAGCAAGACACTGTTGGACACCTCCCTCAA
TCTGGTCAATGCTACTGAACCGGAAAAAGTAGCCATGGGAAAAATCC
AGGATTGCTACAATGAGGCGGGAGTCATAACCAAGATCTCGGATCTG
ATCATCATGGGTACTATCACCACCAGCCCAGAATGCATCAGCCACGCA
CTGAGCACATTGACGACGGATGTTCAAGAAGGCATTTCTAAGCTGAA
CCCTCTGGGGAGATGA (SEQ ID NO: 46)

b)

MKGALLVLALLVTRELGIKMAEACPSFYAVLGVLSLGSKTLLDTSLNLVN
ATEPEKVAMGKIQDCYNEAGVITKISDLIIMGTITTSPECISHALSTLTTD
VQEGISKLNPLGR (SEQ ID NO: 2)

c)

```
Equ c s 2   CPSFYAVLGVLSLGSKTLLDTSLNLVNATEPEKVAMGKIQDCYNEAGVITKISDLIIMGT  60
            CP FY V   ++ G++ LLD SL  VNATEPE+ AM KIQDCY E G+I+++ D ++M T
Fel d 1 2   CPIFYDVFPAVANGNELLLDLSLTKVNATEPERTAMKKIQDCYVENGLISRVLDGLVMTT  83

Equ c s 2   ITTSPECISHALSTLTTDVQEGISKLNPLGR  91
            I++S +C+ A+    D+     KLN LGR
Fel d 1 2   ISSSKDCMGEAVQNTVEDL-----KLNTLGR  109
```

Figure 9
a) IMAC
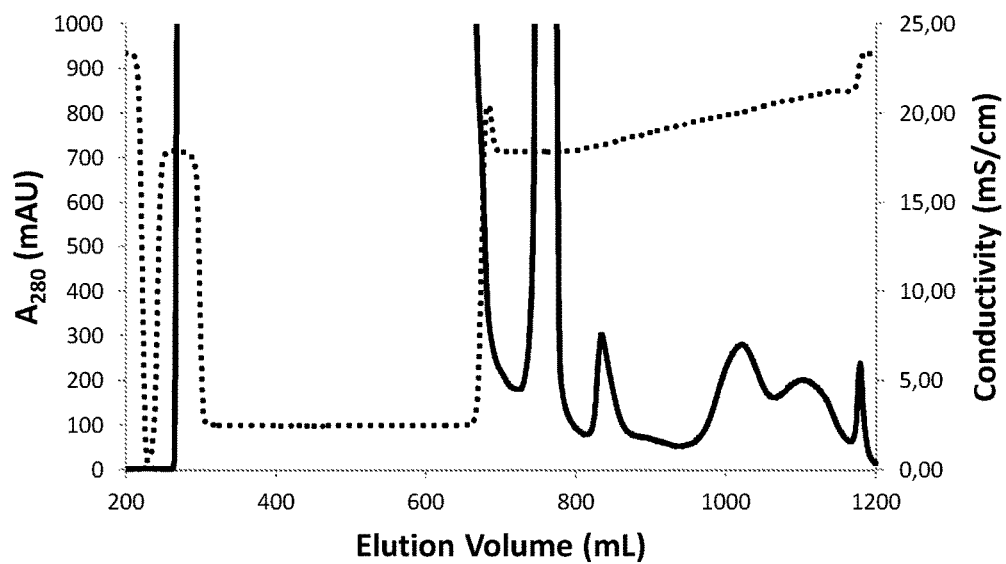
b) AIEC
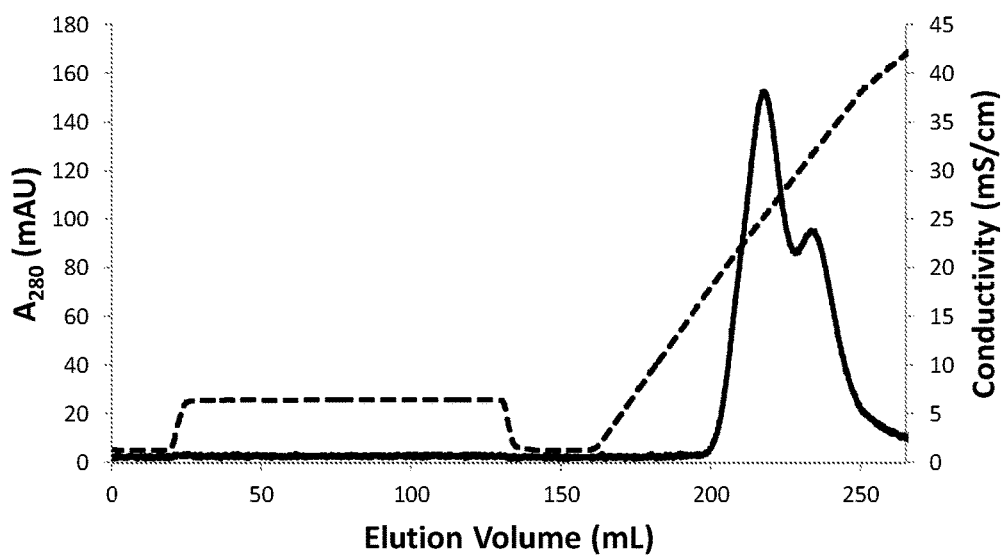

Figure 10:
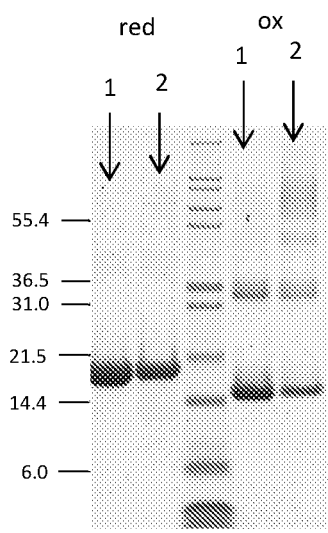

Figure 10
a) Peak 1
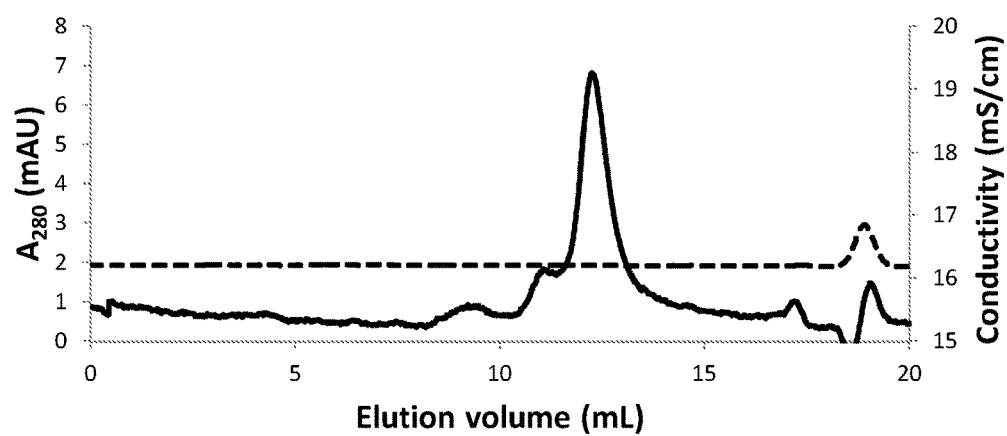
b) Peak 2
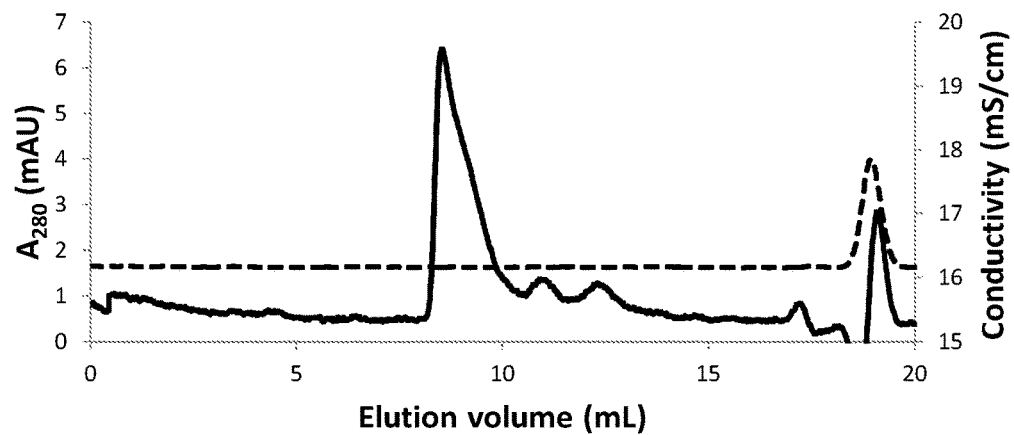

SDS PAGE

ALLERGEN

The Sequence Listing submitted herewith, entitled "pctse2015050828-seql.txt", created Jan. 13, 2017 and having a size of 20,043 bytes, is incorporated herein by reference.

FIELD OF THE INVENTION

The present invention relates to the field of allergy. More specifically, the invention relates to the identification of novel allergens from mammals and to diagnosis and treatment of allergy towards mammals.

BACKGROUND

Approximately 20% of the populations of the industrialized world become hypersensitive (allergic) upon exposure to antigens from a variety of environmental sources. Those antigens that induce immediate and/or delayed types of hypersensitivity are known as allergens (Breiteneder, Hoffmann-Sommergruber et al. 1997). These include products of grasses, trees, weeds, animal dander, insects, food, drugs and chemicals. The antibodies involved in atopic allergy belong primarily to the immunoglobulin E isotype (IgE). IgE binds to basophils mast cells and dendritic cells via a specific high affinity receptor FcεRT. Upon exposure to an allergen, allergen-specific IgE antibodies on the cell surface become cross linked leading to the release of inflammatory mediators such as histamine and leukotrienes resulting in physiological manifestations of allergy (Akdis 2006).

Diagnostic tests for allergy involve the detection of IgE antibodies from patients with a specificity to proteins from an allergen source. However, a positive IgE test, i.e. IgE sensitisation, do not always lead to clinical manifestations of allergy and this discrepancy is one of the main reasons for trying to develop new and better diagnostic procedures. In typical tests, an aqueous extract from the allergen source, containing a mixture of proteins, is used in these tests. For most allergen sources, the allergenic proteins present in crude extract have only partly been identified and characterised. Diagnostic test procedures for detection of specific IgE antibodies in patients can either utilize an in vitro immunoassay using serum from the patient, or be a skin prick test (SPT), performed by topical application of the specific extract on the skin of the patient (Wainstein, Yee et al. 2007). In clinical practice, a doctor's diagnosis of allergy is usually based on both a positive test of IgE sensitisation for the relevant allergen source and a convincing clinical history of allergic reactions to this allergen. In recent years, many important allergenic proteins in the allergenic extracts have been identified and characterized. This has enabled the quantitation of specific IgE antibodies to each of these individual allergenic components, often referred to as component resolved diagnostics (CRD) (Hiller, Laffer et al. 2002) (Valenta, Lidholm et al. 1999) or molecular-based allergy (MA) diagnostics (Canonica, Ansotegui et al. 2013).

It is now widely recognised that Molecular-based allergy (MA) diagnostics has several distinct advantages as compared to conventional IgE analysis using allergen extracts (Canonica, Ansotegui et al. 2013). Analysis of all relevant allergen components from an allergen source has been shown to significantly increase the clinical utility of IgE testing as exemplified by wheat, peanut and hazelnut. (Nicolaou, Poorafshar et al. 2010; Codreanu, Collignon et al. 2011; Ebisawa, Moverare et al. 2012) (Masthoff, Mattsson et al. 2013). A necessary requirement if MA can be applied is that the majority of the individual allergen components from an allergen source has been identified and characterised.

One of the most important implications of MA diagnostics is to distinguish a genuine IgE sensitisation from sensitisation due to cross reactivity which may help the clinician to determine whether a single, a few closely related or several widely different allergen sources are responsible for the allergic symptoms. This can lead to an improved diagnosis of hypersensitivity of pollen (Stumvoll, Westritschnig et al. 2003), venoms (Müller, Schmid-Grendelmeier et al. 2012) and food allergy (Matsuo, Dahlstrom et al. 2008; Ebisawa, Shibata et al. 2012) In particular for peanut and hazelnut allergy, the use of allergen component IgE tests are better at predicting a clinical outcome of allergy than the use of a classical extract IgE test (Nicolaou, Poorafshar et al. 2010; Codreanu, Collignon et al. 2011; Masthoff, Mattsson et al. 2013). One reason for this is that some components may be low abundant and therefore only demonstrate IgE reactivity due to cross reactivity with homologous components from other species. Individuals having only IgE reactivity to such cross reactive components may therefore be less likely to have clinical symptoms to this allergen (Asarnoj, Moverare et al. 2010; Asarnoj, Nilsson et al. 2012). Despite their low clinical association, it is very important to identify all those low abundant cross reactive components in an allergen extract because in the clinical work up of a patient it is important that the sum of IgE reactivities to all components add up to that of the whole extract in order to rule out IgE reactivity to other minor or unknown components in the extract. The outcome of MA diagnostics can thus lead to improved selection of optimal immunotherapy treatment and better risk assessment of different food allergies.

Another use of allergen components is to use these to enhance the diagnostic sensitivity of an extract by spiking the extract with a component. This may be particularly important in miniaturized or non-laboratory immunoassay, such as an allergen microarray or a doctor's office test where the combination of less favourable assay conditions, lower capacity for antibody-binding allergen reagent and natural allergen extract of limited potency, may cause insufficient diagnostic sensitivity.

In conclusion, it is thus of great importance to identify and characterise all important allergenic proteins in each allergen source.

The treatment of allergy is most often reducing symptoms of allergy by e. g. anti-histamines but more long-term and curative treatment of allergy can be performed with specific immunotherapy. Application of the disease causing allergenic extract, most commonly either subcutaneously or sublingually, that causes a specific activation of a protective immune response to the allergenic proteins. Although the exact mechanisms are not fully known, such a specific activation of the immune system alleviates the symptoms of allergy upon subsequent environmental exposure of the same allergen (Akdis and Akdis 2007). A further development of regular immunotherapy has been to use one or several purified allergenic proteins instead of a crude natural extract. Such immunotherapy has been successfully performed for grass pollen allergic patients (Jutel, Jaeger et al. 2005) (Cromwell, Fiebig et al. 2006) (Saarne, Kaiser et al. 2005) and it has also been suggested for treating allergy against animal dander (Valenta, Lidholm et al. 1999; Gronlund, Saarne et al. 2009).

In recent years there has been increasing attention on allergen-specific IgG antibodies. These may modulate the effect of IgE antibodies, either directly by acting as blocking antibodies on the allergen or indirectly by acting via Fc receptors (Akdis and Akdis 2007; Uermosi, Beerli et al. 2010; Uermosi, Zabel et al. 2014).

Thus, by assessing both the specific IgE and the specific IgG response to an allergen may be more clinically relevant than measuring the IgE response alone (Custovic, Soderstrom et al. 2011; Caubet, Bencharitiwong et al. 2012; Du Toit, Roberts et al. 2015). It is well known that immunotherapy induces a specific IgG response which mainly consists of the IgG4 subclass. Since this antibody response is part of the mechanism for successful immunotherapy (Uermosi, Beerli et al. 2010; Uermosi, Zabel et al. 2014), the analysis of allergen specific IgG antibodies may be a way to monitor the efficacy of the treatment.

In conclusion, the measurement of allergen-specific IgG levels may reflect natural or induced tolerance to the allergen through environmental exposure or immunotherapy treatment and may in combination with IgE levels increase the clinical relevance of a diagnostic test.

Horse dander is an increasingly common cause of respiratory allergy (Liccardi, D'Amato et al. 2011), with symptoms including rhinitis, conjunctivitis, bronchial inflammation and asthma. Occupational exposure to horse allergens is a significant risk factor for allergic sensitisation (Tutluoglu, Atis et al. 2002) but considerable concentrations of allergens can be detected also in other places such as schools (Kim, Elfman et al. 2005). IgE sensitisation to horse dander was in one study shown to be associated with a high risk of developing asthma (Ronmark, Perzanowski et al. 2003).

Extracts of horse hair and dander contain a complexity of allergenic proteins and four horse allergens have so far been identified: Equ c 1, Equ c 2, Equ c 3 and Equ c 4. The first two are both members of the lipocalin protein family and have been purified from their natural source (Dandeu, Rabillon et al. 1993; Goubran Botros, Rabillon et al. 1998) while only Equ c 1 has been expressed as a recombinant protein (Gregoire, Rosinski-Chupin et al. 1996). The amino acid sequence of Equ c 1 is 67% similar to that of the cat allergen Fel d 4 (Smith, Butler et al. 2004). Equ c 3, horse serum albumin, is a relatively conserved protein showing extensive cross-reactivity to other mammalian albumins (Goubran Botros, Gregoire et al. 1996). Equ c 4, was first purified (Goubran Botros, Rabillon et al. 1998; Goubran Botros, Poncet et al. 2001) and only later identified as horse sweat latherin (McDonald, Fleming et al. 2009). Recently, a novel horse allergen from the C-D subfamily of the secretoglobin protein family has been characterised (Equ c 15k, WO2011/133105).

Equ c 1 is claimed to be the most important one of the known horse allergens (Dandeu, Rabillon et al. 1993) and IgE antibody recognition of the recombinant protein was present in 76% of a population of horse allergic subjects studied (Saarelainen, Rytkonen-Nissinen et al. 2008). In another study using purified native allergens, only 33% of horse allergic patients were sensitized to Equ c 2 and 23% to Equ c 4 (Goubran Botros, Rabillon et al. 1998). The frequency of IgE binding to horse serum albumin has been addressed in several studies demonstrating reactivity in up to 40% of horse allergic subjects (Spitzauer et al. 1993; Cabañas et al. 2000). However, as sensitization to serum albumins is often accompanied by higher concentrations of IgE antibodies to other allergen components, its specific clinical relevance is uncertain (Spitzauer, Schweiger et al. 1993; Cabañas, López-Serrano et al. 2000). A recent study confirmed the relative prevalence of these horse allergen components and demonstrated a prevalence of 48% of the horse allergic patients having IgE reactivity to Equ c 15k. (WO2011/133105).

SUMMARY OF THE INVENTION

By using sera that were not reactive to any of the known horse allergen components, a novel horse allergen was purified and identified as a secretoglobin. The sequence was partly identified using N-terminal sequencing and MALDI ToF MS. The complete amino acid sequence was verified by 3'RACE and a recombinant single chain protein was produced in E. coli, having similar IgE reactivity as the natural purified protein. The use of the allergen in diagnosis and therapy is also disclosed as well as a diagnostic kit and a pharmaceutical composition containing the allergen.

In a first aspect, the invention relates to an isolated heterodimeric protein having a first peptide chain and a second peptide chain together having an overall sequence identity of at least 70%, such as 75%, 80%, 85%, 90%, 95%, or 98%, with the combined sequences of SEQ ID NO: 3 and SEQ ID NO: 4.

In a further aspect, the invention relates to a single chain protein having an overall sequence identity of at least 70%, such as 75%, 80%, 85%, 90%, 95%, or 98%, with the combined amino acid sequences according to SEQ ID NO: 3 and SEQ ID NO: 4.

In a further aspect, the invention relates to an isolated protein having a sequence identity of at least 70%, such as 75%, 80%, 85%, 90%, 95%, or 98%, with the sequence of SEQ ID NO: 3.

In a further aspect, the invention relates to an isolated protein having a sequence identity of at least 70%, such as 75%, 80%, 85%, 90%, 95%, or 98%, with the sequence of SEQ ID NO: 4.

In a further aspect, the invention relates to a fragment of a protein according to any one of the above aspects comprising at least one IgE antibody epitope of a heterodimeric protein having a first peptide chain having the sequence according to SEQ ID NO: 3 and a second peptide chain having the sequence according to SEQ ID NO: 4.

In a further aspect, the invention relates to a protein or protein fragment according to the above aspects, which has been immobilized to a solid or soluble support. Supports suitable for the immobilization of proteins and peptides are well known in the art, and the present invention encompasses in this aspect any support which does not negatively impact the immunogenic properties of the protein or protein fragment to any substantial extent. In this context, it is understood that the term "immobilized" may be any kind of attachment suitable for a specific support. In one embodiment, the protein or protein fragment according to the invention has been immobilized to a solid support suitable for use in a diagnostic method, such as ImmunoCAP, EliA or VarelisA. In an alternative embodiment, the protein or protein fragment according to the invention has been immobilized to a natural or synthetic polymeric structure in solution, such as one or more dendromeric structures in solution.

In a further aspect, the invention relates to a protein or protein fragment according to the above aspects, which has been provided with a label or a labelling element. Thus, in one embodiment, the invention is a protein or protein fragment according to the invention which has been provided with a luminescent label, such as a photoluminiscent such as a fluorescent or phosphorescent label, a chemiluminescent label or a radioluminescent label. In an alternative embodiment, the protein or protein fragment according to the invention has been derivatized with an element which may be identified, such as an affinity function. Affinity functions for the labelling of proteins and peptides are well known in the art, and the skilled person will be able to choose any suitable function, such as biotin.

In a further aspect, the invention relates to a nucleic acid molecule coding for a protein or protein fragment according to the above aspects, as well as a vector comprising the nucleic acid molecule, a host cell comprising the vector, and a method for recombinant production of a protein or protein fragment according to the above aspects, comprising cultivating the host cell under conditions suitable for expression of the protein.

In a further aspect, the invention relates to a method for in vitro assessment of type 1 allergy comprising the steps of
contacting an immunoglobulin-containing body fluid sample from a patient suspected of having Type 1 allergy with a protein, peptide chain or protein fragment according to the above aspects; and
detecting the presence, in the sample, of antibodies, such as IgE antibodies specifically binding to said protein, peptide chain or protein fragment;
wherein the presence of antibodies such as IgE antibodies is informative of a Type 1 allergy in said patient.

In one embodiment, the method according to the invention comprises detecting the presence, of IgE and/or IgG antibodies specifically binding to said protein, peptide chain or protein fragment. In other embodiment(s), the present invention uses other or additional isotypes of antibodies such as IgA; IgD; and/or IgM. In this embodiment, the presence of specific IgE antibodies is indicative of a Type 1 allergy to horse in said patient and the level of specific IgG antibodies is informative in regard to natural or induced tolerance to horse through environmental exposure or immunotherapy treatment.

In one embodiment, this method according to this aspect further comprises the steps of
contacting the immunoglobulin-containing body fluid sample from the patient suspected of having Type 1 allergy with at least one further purified allergen component from horse; and
detecting the presence, in the sample, of IgE antibodies specifically binding to said purified allergen component from horse;
wherein the combination of presence of IgE antibodies specifically binding to said protein, peptide chain or protein fragment, and absence of IgE antibodies specifically binding to said allergen component from horse, is indicative of a Type 1 allergy to cat in said patient.

In this embodiment, the further purified allergen component from horse is preferably selected from the group consisting of native and recombinant Equ c 1, Equ c 2, Equ c 3, Equ c 4/5, and Equ c 15k.

In a further aspect, the present invention relates to an assay using labelled and/or immobilized proteins and/or protein fragments as described in the present application. In one embodiment, the invention is an assay comprising the steps of (i) capturing of an antibody isotype of interest on a solid or soluble support as discussed above; (ii) adding a protein or protein fragment according to the invention; and (iii) direct or indirect detection of the binding of protein or protein fragment to the antibody. In one embodiment, the protein or protein fragment has been labelled with a fluorophore, in which case the detection is a direct detection. In another embodiment, the protein or protein fragment has been derivatized as discussed above, e.g. by an enzyme-conjugated element such as avidin or streptavidin.

Thus, the present invention is useful in a number of different types of IgE and IgG assays, such as in a reverse assay where for example IgE antibodies obtained from an IgE sensitised subject are captured on a support and detected by binding to a labelled allergen, as discussed above.

In a further aspect, the invention relates to a kit for performing the methods according to the above aspects, said kit comprising a protein, peptide chain, or protein fragment according to the invention immobilised on a solid support.

In one embodiment of this aspect the solid support is selected from the group of nitrocellulose, glass, silicon, and plastic and/or is a microarray chip.

In one embodiment of this aspect the kit further comprises a detecting agent capable of binding to antibodies, such as IgE antibodies and/or IgG antibodies bound to the immobilised protein, peptide chain, or protein fragment. Such detecting agents may e.g. be anti-IgE antibodies labelled with detectable labels, such as dyes, fluorophores or enzymes, as is known in the art of immunoassays.

Aspects of the invention further include proteins or protein fragments according to the aspects above for use in methods for therapy or diagnosis practised on the human or animal body, such as therapy or diagnosis of Type 1 allergy practised on the human or animal body, and methods for treatment of Type 1 allergy, comprising administering, to an individual susceptible to such treatment, a protein, peptide chain, or protein fragment according to the above aspects.

Definitions

The terms "protein" and "peptide" should be construed to have their usual meaning in the art. The terms are used interchangeably herein, if not otherwise stated.

The "length" of a protein is the number of amino acid residues in the protein.

A "fragment" of a protein should be construed as meaning a protein fragment consisting of at least 10 amino acids, or having a length of at least 10% of the length of original protein. Fragments include protein fragments with a length of at least 20%, 30%, 40%, 50%, 60%, 70%, 80%, and 90% of the full length of the original protein.

A "variant" of a protein relates to a variant of an original protein having a sequence identity to said original protein of at least 70%, preferably over 75%, 80%, 85%, 90%, 95%, or 98%, calculated over the entire length of the variant protein. A number of software tools for aligning an original and a variant protein and calculating sequence identity are commercially available, such as Clustal Omega provided by the European Bioinformatics Institute (Cambridge, United Kingdom). Protein variants may have a length of 10%, 20%, 30%, 40%, 50%, 60%, 70%, 80%, 90%, 95%, 98%, 100%, 105%, or 110% of the original protein. Protein variants may thus comprise additional amino acids as a result of their production, such as a hexahistidine tag, linker sequences, or vector derived amino acids. In order to be a "variant" of an original allergenic protein, the variant protein should preferably also comprise at least one IgE antibody epitope of the original allergenic protein, i.e. bind IgE antibodies from a serum sample from a representative patient sensitized to the original allergenic protein. Whether a variant of an original allergenic protein comprises an IgE antibody epitope of the original allergenic protein can be assayed by using the inhibition assay described in Example 10. Variants comprising an IgE binding epitope of the original IgE binding epitope are those molecules that causes a "significant inhibition" of the binding to the original protein which should be construed as those molecules that can inhibit the binding by at least 10%, 20%, 30% 40% or 50% compared to inhibition by buffer alone (IgE diluent, Thermo Fisher Scientific).

Preferably, the variant binds IgE antibodies at substantially the same level as the original allergenic protein. Binding levels can be measured by immobilising the variant or fragment on a solid phase and measuring the IgE reactivity of individual sera as is described in Example 8. For the purposes of this definition, "substantially the same level" should be construed as meaning that the binding level of the variant differs from the binding level of the original protein by at most 25%, 20%, 15%, 10%, or 5%.

A "heterodimeric protein" relates to a protein that in its native form comprise two protein chains with different amino acid sequences, bound together by covalent or non-covalent bonds. The monomer units, i.e. the protein chains, may be encoded by one gene or separate genes in the organism of origin.

"Sequence identity" relates to the extent to which two (nucleotide or amino acid) sequences have the same residues at the same positions in an alignment, expressed as a percentage. "Alignment" in this regard relates to the process or result of matching up the nucleotide or amino acid residues of two or more biological sequences to achieve maximal levels of identity and, in the case of amino acid sequences, conservation, for the purpose of assessing the degree of similarity and the possibility of homology. In case of a heterodimeric protein, the amino acid sequences of the respective chains, or the nucleic acid sequences encoding them, may be concatenated and used in the alignment in order to determine an "overall" sequence identity. See also Fassler and Cooper, "BLAST Glossary", in BLAST® Help, Bethesda (Md.): National Center for Biotechnology Information (US); 2008-.

The term "vector" relates to a DNA molecule used as a vehicle to artificially carry foreign genetic material into another cell, where it can be replicated and/or expressed.

BRIEF DESCRIPTION OF DRAWINGS

FIG. 1 shows the fractionation of horse dander proteins by size exclusion chromatography (SEC) where $A_{280}$ absorbance is indicated by solid line and conductivity is indicated by a hatched line. Arrows indicate the position of the fractions that were tested for IgE reactivity. Vertical bars indicate the pool containing the active fraction that was subjected to further purification.

FIG. 2 shows the second purification step of the unknown horse dander component by hydrophobic interaction chromatography where $A_{280}$ absorbance is indicated by solid line and the percentage of Tris pH 8.0 buffer in pump B (% B) is indicated by a hatched line. Arrows indicate the position of the fractions that were tested for IgE reactivity. Vertical bars indicate the pool containing the active fraction that was subjected to further purification.

FIG. 3 shows the third purification step of the unknown horse dander component by anion exchange chromatography where $A_{280}$ absorbance is indicated by solid line and conductivity is indicated by a hatched line. Arrows indicate the position of the fractions that were tested for IgE reactivity. Horizontal bars indicate the pools that were further tested of which one contained the active fraction that was subjected to further purification.

FIG. 4 shows the fourth purification step of the unknown horse dander component by reversed phase chromatography where $A_{280}$ absorbance is indicated by solid line and the percentage of 0.05% TFA 90% acetonitril buffer in pump B (% B) is indicated by a hatched line. Vertical bars indicate the pooling of the three peaks (labelled 1, 2 and 3) that each was subjected to SDS PAGE analysis and tested for IgE reactivity.

FIG. 5 shows SDS-PAGE analysis of reduced and non-reduced samples of the three peaks from the RPC purification step. Lane M contains molecular weight marker proteins with the molecular weights indicated to the left.

FIG. 6 shows the postulated nucleotide (a) and amino acid (b) sequence of the full length protein Equ c s chain 1. In (c) the amino acid alignment with the homologous molecule Fel d 1 chain 1 from cat is shown.

FIG. 7 shows the postulated nucleotide (a) and amino acid (b) sequence of the full length protein Equ c s chain 2. In (c) the amino acid alignment with the homologous molecule Fel d 1 chain 2 from cat is shown.

FIG. 8 shows the RPC purification step of an anion exchange chromatography pool, performed using a steeper gradient in order to increase the concentration of protein in the fractions. Vertical bars indicate the fractions D4 and D5 that were subjected to MS/MS in-solution digestion analysis.

FIG. 9 shows the purification of recombinant Equ c s by IMAC (a) where $A_{280}$ absorbance is indicated by solid line and conductivity is indicated by a hatched line. The imidazol elution gradient ranges from 800-1200 mL. Arrows indicate the peak that was pooled and subjected to anion exchange chromatography (b). Arrows indicate the peak 1 and 2 and vertical bars indicate the limits of these pools.

FIG. 10 shows analytical gel filtration analysis of recombinant Equ c s ab where $A_{280}$ absorbance is indicated by solid line and conductivity is indicated by a hatched line. In (a) analysis of rEqu c s ab, peak 1 from AIEC, and in (b) rEqu c s ab, peak 2 from AIEC, is shown. In (c) SDS PAGE analysis of recombinant Equ c s ab of peak 1 and peak 2 from AIEC under both reducing and non-reducing conditions is shown.

FIG. 11 shows the correlation between the IgE reactivity of native and recombinant Equ c s in 35 horse dander sensitised subjects. The 0.35 $kU_A$/L and 0.1 $kU_A$/L levels are indicated by dotted lines.

FIG. 12 shows levels of IgE antibodies to horse dander extract (HDE), Equ c 1, nEqu c 2, nEqu c 3. nEqu c 4, rEqu c 15k and rEqu c s in a cohort of 25 horse dander allergic subjects. The number of observations below 0.1 $kU_A$/L is indicated in brackets for each component. Dotted line indicates the 0.35 $kU_A$/L level and solid line indicates the 0.1 $kU_A$/L level. Horizontal bars indicate median levels of IgE.

FIG. 13 compares IgE antibody binding to rEqu c s and rFel d 1 in a cohort of horse dander sensitised subjects. The 0.35 $kU_A$/L and 0.1 $kU_A$/L levels are indicated by dotted lines.

SEQUENCE LISTING

The following sequences are listed in the sequence listing.

| SEQ ID NO: | Description |
|---|---|
| 1 | amino acid sequence of the 5 kDa chain of Equ c s including signal peptide |
| 2 | predicted amino acid sequence of the 10 kDa chain of Equ c s including signal peptide |
| 3 | predicted amino acid sequence of the 5 kDa chain of Equ c s |
| 4 | predicted amino acid sequence of the 10 kDa chain of Equ c s |
| 5 | amino acid sequence for the whole recombinant protein rEqu c s ab |

-continued

| SEQ ID NO: | Description |
|---|---|
| 6 | nucleic acid sequence encoding the whole recombinant protein rEqu c s ab |
| 7 | amino acid sequence for the alternative recombinant protein rEqu c s ba |
| 8 | nucleic acid sequence encoding the alternative recombinant protein rEqu c s ba |
| 9 | Codon optimized nucleic acid molecule encoding chain 1 |
| 10 | Codon optimized nucleic acid molecule encoding chain 2 |
| 11 | Forward primer for chain 1, PCR 1 |
| 12 | Forward primer for chain 2, PCR 1 |
| 13 | Forward primer for chain 1, PCR 2 |
| 14 | Forward primer for chain 2, PCR 2 |
| 15 | Reverse primer for chain 1, PCR 2 |
| 16 | Reverse primer for chain 2, PCR 2 |
| 17-33 | Peptide fragments disclosed in Table 7 |
| 34-43 | Peptide fragments disclosed in Table 8 |
| 44 | Double sequence given by N-terminal sequencing analysis by Edman degradation of the RPC peak 2 |
| 45 | The complete DNA sequence of the postulated sequence denoted Equ c s, chain 1 |
| 46 | The complete DNA sequence of the postulated sequence denoted Equ c s, chain 2 |
| 47 | Fel d 1 chain 1 |
| 48 | Fel d 1 chain 2 |

DETAILED DESCRIPTION OF THE INVENTION

In one aspect the present invention relates to an isolated horse allergen, herein denoted Equ c s, belonging to the secretoglobin family, showing an electrophoretic mobility (apparent molecular weight) corresponding to approximately 18 kDa under non-reducing conditions, and comprising a first peptide chain having a molecular weight in the order of 5 kDa and a second peptide chain having a molecular weight in the order of 10 kDa, linked together by one or more disulphide bonds. This aspect of the invention also comprises variants and fragments of Equ c s with certain sequence identity to native Equ c s, as defined above, and preferably comprising at least one IgE antibody epitope of native Equ c s. Such variants and fragments preferably have IgE reactivity to Equ c s reactive sera and at least 10% of the IgE binding to the original rEqu c s molecule can be inhibited by such a variant or fragment, as determined by the assay described in Example 10. Also in the other aspects of the invention described below, the term "Equ c s" is, for simplicity, used to also include such variants and fragments thereof.

In another aspect, the invention relates to an isolated nucleic acid molecule encoding the allergen according to the first-mentioned aspect, as well as to a vector containing the nucleic acid molecule, and to a host cell containing the vector. Recombinant proteins or peptides produced by such a vector-containing host cell may be glycosylated or not depending on the host cell used.

In a further aspect, the invention relates to an in vitro method for assessment of a Type I allergy in a patient, wherein a body fluid sample, such as a blood or serum sample from the patient, is brought into contact with Equ c s or a composition according to the previous aspect, whereby it can be determined whether or not the patient sample contains IgE antibodies that bind specifically to the Equ c s. Such a method may be carried out in any manner known in the art. The Equ c s may e.g. be immobilized on a solid support, such as in a conventional laboratory immunoassay, in a microarray or in a lateral flow assay, or used as a fluid-phase reagent.

In yet a further aspect, the invention relates to an in vitro method for assessment of a Type I allergy in a patient, wherein a body fluid sample, such as a blood or serum sample from the patient, is brought into contact with Equ c s, whereby it can be determined whether or not the patient sample contains IgE antibodies that bind specifically to the Equ c s but not to other horse allergen components, such as Equ c 1, Equ c 2, Equ c 3, Equ c 4/5 or Equ c 15k. A patient showing IgE reactivity against Equ c s, but not against other horse allergen components, is likely to be primarily sensitised to cats and not to horses.

In the above mentioned aspects, the wildtype Equ c s molecule may, as mentioned above, be replaced with fragments or variants of Equ c s, natural or man-made, comprising IgE antibody epitopes from the wildtype protein.

The invention further relates to a method of treatment of Type I allergy comprising administering to a patient in need of such treatment Equ c s or a modified Equ c s, as explained below. This aspect of the invention also relates to the use of the Equ c s in such immunotherapy, including e.g. component-resolved immunotherapy (Valenta and Niederberger 2007). In one embodiment of this aspect, the Equ c s may be used in its natural form or in a recombinant form displaying biochemical and immunological properties similar to those of the natural molecule. In another embodiment, the Equ c s may be used in a modified form, generated chemically or genetically, in order to abrogate or attenuate its IgE antibody binding capacity, while preferably being capable of eliciting an IgG response in a treated individual. Examples of modifications include, but are not limited to, fragmentation, truncation, tandemerization or aggregation of the molecule, deletion of internal segment(s), substitution of amino acid residue(s), domain rearrangement, or disruption at least in part of the tertiary structure by disruption of disulfide bridges or its binding to another macromolecular structure, or other low molecular weight compounds. In yet another embodiment of this aspect, the individual 10 kDa and/or 5 kDa subunits of Equ c s are used as modified Equ c s.

In all of the above mentioned aspects of the invention, the Equ c s protein may be purified from its natural source, such as from urine, saliva or other body fluids, or from tissue, such as hair or dander, from horse. It may also, as mentioned above, be produced by recombinant DNA technology or chemically synthesized by methods known to a person skilled in the art or described in the present application.

The allergenic horse protein described here, Equ c s, belongs to the secretoglobin protein family, specifically one subfamily which comprises tetrameric proteins formed by two heterodimeric subunits. The heterodimer consists of two chains derived from different genes linked together by disulfide bridges (Klug et al. 2000). The horse secretoglobin described here is a 18±2 kDa heterodimer, herein referred to as Equ c s, consisting of a 5±2 kDa and a 10±2 kDa subunit, respectively, which for the purposes of this invention are referred to as the 5 and 10 kDa subunits, respectively. The molecular weight assignments are according to their apparent molecular weight as observed in SDS-PAGE, as described in Example 3 below. It is understood that the apparent molecular weights will vary depending on the separation conditions, including electrophoretic separation medium and concentration thereof, linear or gradient buffer used, etc. Also, the 10 kDa subunit contains an N-glycosylation site, the occupation of which by a glycan structure may affect the apparent molecular weight.

The amino acid sequence of the 5 kDa chain has the predicted amino acid sequence

```
                                                                      (SEQ ID NO: 3)
DICPAVKEDV NIFLTGTPDD YVKKVSQYQR NPVILANAEK LKNCIDKKLT AEDKENALSV     60

LEKIYSSDFC                                                           70
``` and a theoretical molecular weight of 7.9 kDa.

The amino acid sequence of the 10 kDa chain has the predicted amino acid sequence

```
                                                                      (SEQ ID NO: 4)
CPSFYAVLGV LSLGSKTLLD TSLNLVNATE PEKVAMGKIQ DCYNEAGVIT KISDLIIMGT     60

ITTSPECISH ALSTLTTDVQ EGISKLNPLG R                                   91
``` and a theoretical molecular weight of 9.6 kDa.

It is to be noted that structurally related proteins have been described in a wide range of mammalian species but only two proteins have been defined as allergens, the major cat allergen Fel d 1 (Acc no P30438 and P30440) and Equ c 15k (WO2011/133105).

Although the horse dander allergens Equ c 1, Equ c 2, Equ c 3, Equ c 4/5 and Equ c 15k cover most of the IgE reactivity to horse dander extract observed in horse allergic patients, we have encountered several cases of cat allergic individuals demonstrating IgE reactivity to horse dander extract without concomitant reactivity to any of the five known horse allergen components. This invention describes the identification and characterisation of the horse allergen responsible for this unknown IgE reactivity to horse dander extract leading to the discovery of a protein homologue to the cat allergen Fel d 1.

In a collection of sera from cat sensitised subjects a number of sera could be characterised having reactivity to horse dander extract while no reactivity to any of the known horse dander allergens could be detected. Using the sera described above, the IgE binding to horse dander extract could be inhibited by recombinant Fel d 1, indicating that the IgE reactivity is directed to a horse protein that is immunologically similar to Fel d 1.

With the aid of these sera, a new major allergen could be purified from horse dander and identified as a member of the secretoglobin protein family. The novel horse protein, herein referred to as Equ c s, consists of one 5 kDa amino acid chain and one 10/11 kDa amino acid chain joined together by disulfide bridges. Considering the fact that the two polypeptide chains are encoded by separate genes, this study demonstrates the presence of a heterodimeric protein that has not previously been anticipated by bioinformatic studies of the horse genome. It is distinct from previously known horse allergens. This allergen represents an important addition to the panel of known horse allergens and will be useful in the diagnosis of horse allergy. Since this is an allergen that is cross reactive to the main cat allergen Fel d 1, IgE reactivity to this molecule may reflect cross reactive sensitisation to horse dander that may or may not be associated to clinical symptoms.

The examples below illustrate the present invention with the isolation and use of the secretoglobin denoted Equ c s from horse. The examples are only illustrative and should not be considered as limiting the invention, which is defined by the scope of the appended claims.

Example 1: Identification of Sera Detecting an Unknown Allergen Component in Horse Dander Extract that is Similar to Fel d 1

Horse dander extract, cat dander extract and Fel d 1 regular ImmunoCAP tests were used. Experimental immunoCAP tests using recombinant Equ c 1 and Equ c 15k as well as Equ c 2 and Equ c 4 purified from horse dander and Equ c 3 purified from horse serum were produced essentially as described in Patent WO2011/133105).

A collection of sera having high level of sensitisation to cat dander extract were tested for IgE reactivity to cat and horse dander components. The five sera identified here were characterised by high IgE reactivity to cat dander extract, Fel d 1 and horse dander extract without concomitant reactivity to any of the five known horse allergen components (table 1). These sera thus detected an unknown allergen component in horse dander extract.

The selected sera were utilised in inhibition tests using both horse dander extract and cat dander extract as solid phase (table 2). As inhibitors recombinant Equ c 15k, Fel d 1 and Fel d 7 respectively were used at a final concentration of 100 µg/ml. As an inhibition control buffer, 0.1 M sodium phosphate buffer, pH 7.4, containing 0.3% human serum albumin was used. Means of duplicate determinations of each inhibition were calculated and the fraction of inhibition was calculated as the fraction of the binding using inhibition control buffer that could be quenched with each inhibitor. In these selected sera, binding to cat dander extract could be almost completely inhibited by Fel d 1 (table 2a). None of the other inhibitors tested showed any inhibition. This demonstrates that the IgE binding to cat dander extract is dominated by reactivity to Fel d 1. Likewise, the binding to horse dander extract solid phase (table 2b) could be fully inhibited by rFel d 1 but none of the other inhibitors. This demonstrated that the binding to horse dander extract by these sera is directed to a horse dander component that is immunologically similar to the cat allergen Fel d 1. Although Equ c 15k belongs to the secretoglobin family this protein did not demonstrate any inhibition of the binding to horse dander extract, indicating that the horse component searched for is not Equ c 15k. This can be explained by the fact that the two proteins belong to different sectretoglobin subfamilies, Fel d 1 belongs to the B-E subfamily and Equ c 15k belongs to the C-D subfamily (Laukaitis and Karn 2005), WO2011/133105

Example 2: Purification of a Horse Dander Allergen Component, Homologous to the Cat Allergen Fel d 1

By use of the sera described in example 1, an unknown allergen component, similar to Fel d 1, could be detected in horse dander extract and by fractioning horse dander extract by chromatographic procedures and immobilising these fractions on an ImmunoCAP solid phase, the unknown component could be followed during several chromatographic steps.

Size Exclusion Chromatography

Horse dander (Allergon, Välinge, Sweden) was extracted in 20 mM MOPS, pH 7.6, 0.15 M NaCl (MBS=MOPSbuffered saline), clarified by centrifugation and filtered through a 0.45 µm mixed cellulose ester filter (Millipore, Billerica, Mass., USA). As a first purification step, the clarified extract was applied to a Superdex™ 75 column (XK26/100, $V_t$=505 mL, GE Healthcare Bio-Sciences AB, Uppsala, Sweden) for size exclusion chromatography (SEC) and elution was performed with MBS at a flow rate of 2 mL/min.

The chromatogram is shown in FIG. 1 in which six fractions, indicated by arrows, were immobilised on solid phase as described previously (Marknell DeWitt, Niederberger et al. 2002). The IgE binding using the sera described above to the immobilised fractions are shown in table 3 which indicates that the tested fractions 18, 22 and 26 contain the highest amounts of the unknown allergen component. Fractions 16-27 (indicated with vertical bars in FIG. 1) were pooled and subjected to hydrophobic interaction chromatography.

Hydrophobic Interaction Chromatography

Figure 2:
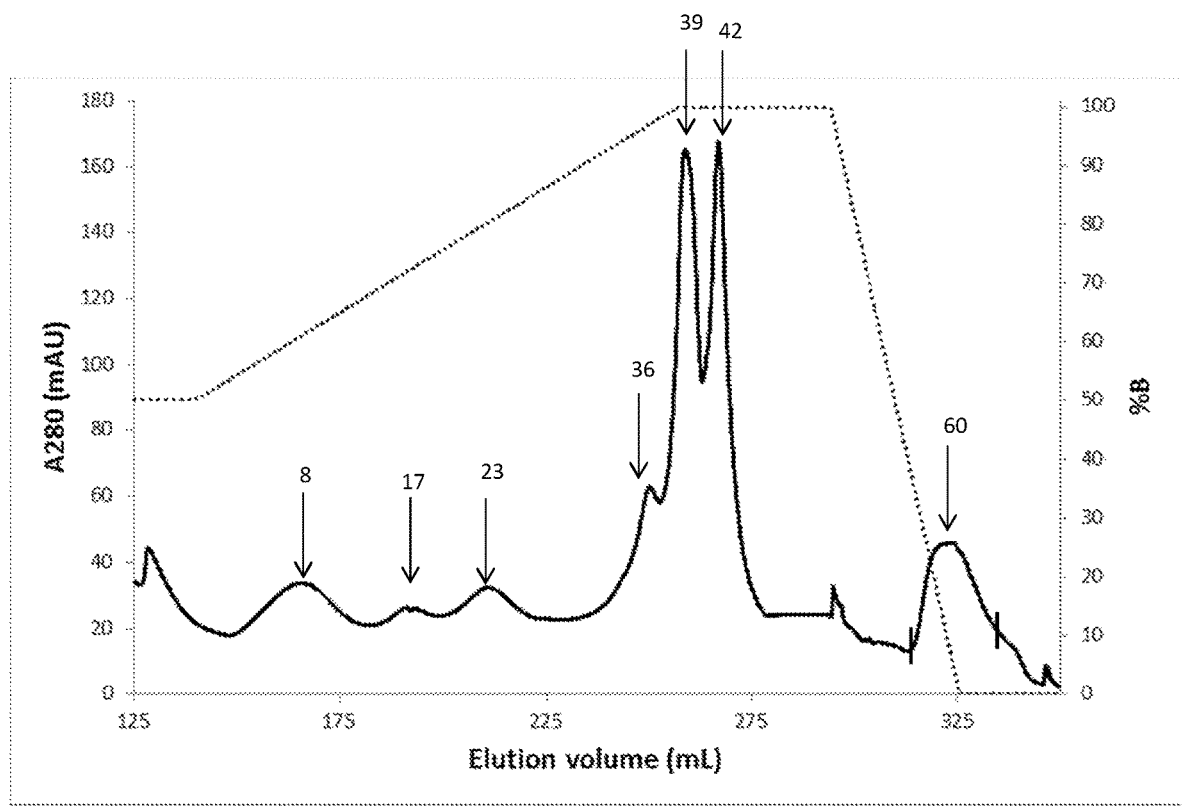

The pool from SEC was adjusted to 1 M $NH_4SO_4$ and applied to a Phenyl Sepharose™ HP column (HR10/10, $V_t$=8.0 mL, GE Healthcare Life Sciences) equilibrated with 1 M $NH_4SO_4$ in 20 mM tris pH 8.0. Elution was performed in a linear $NH_4SO_4$ gradient from 1 M to 0 M $NH_4SO_4$ (indicated as 50%-100% B in the chromatogram in FIG. 2 between elution volumes 140 to 260 mL). In order to elute strongly bound proteins, the pump A was washed and the buffer was changed to 30% isopropanol in 20 mM Tris pH 8.0. An isopropanol gradient from 0-30% isopropanol was then used to elute remaining protein on the column (indicated as a gradient from 100%-0% B on the chromatogram between elution volumes 285 and 325 mL). Seven peaks, indicated in the chromatogram, were diluted 1:2 in coupling buffer (0.1M $NaHCO_3$, pH8.0), immobilised on Immuno-CAP solid phase and tested for IgE reactivity using the previously described detector sera (table 4). The highest IgE reactivity was obtained in the isopropanol wash gradient in fraction 60. Fractions 58-66 were pooled and subjected to anion exchange chromatography.

Anion Exchange Chromatography

Figure 3:
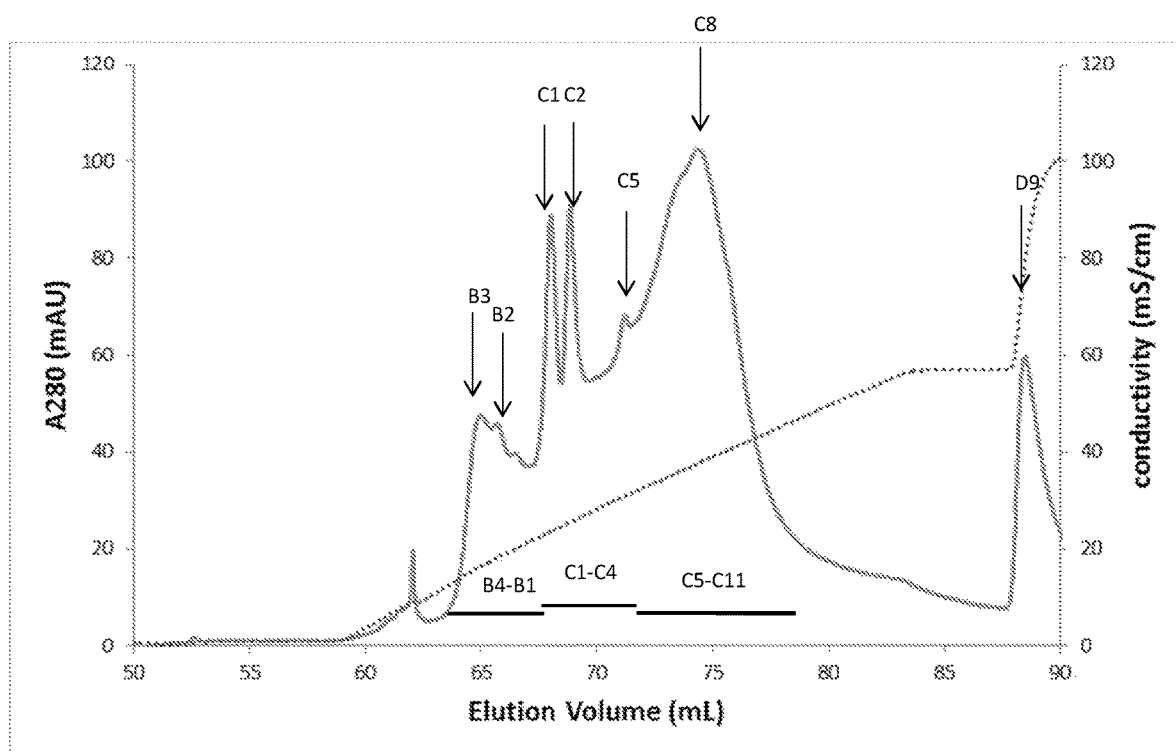

The HIC pool was conditioned by adding half the volume of the pool of Tris pH 8.5 to the HIC pool. The pool was subsequently applied to an anion exchange column Source™ 15Q (PE4.6/100, $V_t$=1.66 mL, GE Healthcare Life Sciences) equilibrated with 20 mM Tris, pH 8.5. Upon elution in a linear 0-0.50 M NaCl gradient in the same buffer the protein was resolved into several peaks (FIG. 3) of which seven were immobilised after dilution 1:4 in coupling buffer. Since IgE reactivity to the unknown component was detected in most of the fractions at this dilution (table 5a), three pools, B4-B1, C1-C4 and C1-C11, were pooled based on protein band pattern on SDS PAGE and immobilised after dilution 1:20 in coupling buffer. IgE analysis of the more diluted pooled fractions revealed that the highest activity (table 5b) was found in the first pool, B4-B1 which was subjected to a final chromatographic RPC purification step.

Reversed-Phase Chromatography

The anion exchange pool was conditioned by adding TFA to a final concentration of 0.065% and subjected to a final RPC purification step by applying the sample to a Source™ 15 RPC column (Resource, $V_t$=3.2 mL; GE Healthcare Life Sciences) equilibrated with 0.065% TFA in water. Elution was performed in a linear 0-60% gradient of buffer B, consisting of 0.05% TFA in 90% acetonitrile. A Three peaks were eluted near the end of the gradient (FIG. 4) that were immobilised on solid phase and tested. According to table 6 the two first peaks contained high levels of the unknown component of which peak no 2 contained slightly more than the first peak.

Example 3: Analysis of the Purified Fraction by SDS PAGE, N-Terminal Sequencing and MALDI TOF MS SDS PAGE analysis of the RPC fractions revealed a similar pattern for the first two RPC peaks, one 5 kDa band and a double band at 10/11 kDa under reducing conditions that came together at a broad band at 18 kDa under non-reducing conditions. This band pattern is consistent with proteins from the secretoglobin family that typically contain two bands at 5 and 10 kDa under reducing conditions and one band at 15-20 kDa under non-reducing conditions. The largest of the two bands band is glycosylated and therefore may appear diffuse or as in this case appear as a double band.

N-terminal sequencing analysis by Edman degradation of the RPC peak 2, performed essentiallly as described in (Mattsson, Lundgren et al. 2009), revealed a double sequence that became less clear after seven residues:
Amino acid residue no: 1 2 3 4 5 6 7
First alternative D P S F Y A V
Second alternative - I R P A V -

Since the relative amounts of the amino acids in each cycle were similar it was not possible to establish a primary and a secondary sequence from these data. The double sequence is also shown in the sequence listing as in SEQ ID NO: 44.

In gel digestion with trypsin on spots from one dimensional SDS PAGE gel electrophoretic bands 5, 10 and 11 kDa followed by analysis by matrix assisted laser desorption ionization time of flight mass-spectrometry (MALDI TOF MS) using a Bruker Daltonics Autoflex 2 instrument (Bruker Daltonics, Bremen, Germany) followed by peptide mass fingerprint (PMF) analysis did not result in significant matches with any known proteins in the NCBI-NR database except for the 5 kDa band that matched a predicted sequence of an uncharacterised horse protein (XP_005596696). However, although a part of the sequence of this record was homologous to secretoglobins, the molecular weight was too high for this family of molecules and did not match the band that it was picked out from. It was assumed that this predicted record was faulty.

Example 4: Bioinformatic Analysis of Horse Genomic Sequences Identifying Amino Acid Sequences Homologous to Chain 1 and Chain 2 of Fel d 1

Chain 1

The cat allergen protein Fel d 1, which was immunologically similar to the unknown horse dander protein as demonstrated in example 1, consists of two amino acid chains, chain 1 and chain 2 (acc no: NP_001041618 and NP_001041619 respectively) joined together by disulfide bridges.

A TBLASTN search of a horse genome database (wsg) with the sequence of Fel d 1, chain 1 (NP_001041618) resulted in a match of aa 17-79 to the translation of nucleotide positions 77633-77453 (of the reverse strand) of Acc No. AAWR02030062, a 105199 bp segment of the horse genome sequence.

A larger segment surrounding this sequence, 90000-70021 of Acc No. AAWR02030062 was fed into the gene finding program FGENESH+ together with the precursor sequence of Fel d 1 chain 1. The program searches for homologous genes within a genomic sequence.

The result was a postulated sequence consisting of three exons Acc No. AAWR02030062:
77850→77790
77632→77445
76428→76399

The complete DNA sequence of this postulated sequence, denoted Equ c s, chain 1, is shown in FIG. 6a (SEQ ID NO: 45) encoding 92 amino acid residues (SEQ ID NO: 1, FIG. 6b), of which the first 22 residues were predicted by SignalP to form a signal peptide. The mature protein deduced from the cloned cDNA consisted of 70 amino acid residues, including three cysteins, and had a predicted molecular mass of 7.9 kDa and an isoelectric point of 4.96. A protein BLAST homology search using this predicted sequence reveals an amino acid sequence with homology to secretoglobins. The predicted sequence has 67% amino acid identity to Fel d 1 chain 1 (SEQ ID NO: 47) (FIG. 6c).

Chain 2

Similarly to above A TBLASTN search of a horse genome database (wsg) with the sequence of Fel d 1, chain 2 (NP_001041619) resulted in a match of aa 21-85 to the translation of nucleotide positions 82588-82782 (of the forward strand) of Acc No. AAWR02030062, a 105199 bp segment of the horse genome sequence.

A larger segment surrounding this sequence, 70021-94020 of Acc No. AAWR02030062 was fed into the gene finding program FGENESH+ together with the precursor sequence of Fel d 1 chain 2. The program searches for homologous genes within a genomic sequence.

The result was an incomplete postulated sequence consisting of two exons from Acc No. AAWR02030062:
82004→82064
82589→82770

Based on homology with the sequence for Fel d 1 chain 2, the last exon is missing in this postulated sequence. A protein BLAST search comparing exon 3 of Fel d 1 chain 2 with the translated genomic sequence following nukleotide 82770 identified a genomic sequence having homology to exon 3 of Feld 1 chain 2. This postulated exon 3 of Equ c s could be joined in frame with the previous exons and contained a stop codon at an homologous position to exon 3 of Fel d 1 chain 2. The sequence of this final exon was found at: 90025-90127 of the genomic sequence Acc No. AAWR02030062.

The complete DNA sequence of this postulated sequence, denoted Equ c s, chain 2, is shown in FIG. 7a (SEQ ID NO: 46) encoding 114 amino acid residues (SEQ ID NO: 2, FIG. 7b), of which the first 23 residues were predicted by SignalP to form a signal peptide. The mature protein deduced from the cloned cDNA consisted of 91 amino acid residues, including three cysteins, and had a predicted molecular mass of 9.6 kDa and an isoelectric point of 4.84. A protein BLAST homology search using this predicted sequence reveals an amino acid sequence with homology to secretoglobins. The predicted sequence has 47% amino acid identity to Fel d 1 chain 2 (SEQ ID NO: 48) (FIG. 7c).

Example 5: PCR Amplification and Sequencing of Equ c s Chain 1 and Chain 2 mRNA from Horse Skin Total RNA was prepared from horse skin using the RNAqueous kit (Ambion, Austin, Tex., USA). Polyadenylated RNA was isolated from total RNA using the mRNA Purification kit and first strand cDNA was prepared using the First-Strand cDNA Synthesis kit (both from Thermo Fisher Scientific). 3' RACE was performed according to Frohman (Frohman 1993), using a gene-specific forward oligonucleotide primer from the untranslated sequence before the starting codon,

```
                                    (SEQ ID NO: 11, chain 1)
    5'-ATAAAAGGGCTGCAGAATTG-3'
    and (SEQ ID NO: 12, chain 2)
    5'-GCAGCAGAAACCCTGCCCTG-3'.
```

A second PCR was performed using a second gene-specific forward oligonucleotide primer from the untranslated sequence before the starting codon,

```
                                    (SEQ ID NO: 13, chain 1)
    5'-GTGAGCACCTGCCACCTG-3'
    and (SEQ ID NO: 14, chain 2)
    5'-GAAGAGCATTCTAGCAGTTG-3'
``` carrying a terminal NdeI restriction site for cloning and specific reverse oligonucleotide primers,

```
                                    (SEQ ID NO: 15, chain 1)
    5'-GAATCTTCTAATCAGACAC-3'
    and (SEQ ID NO: 16, chain 2)
    5'-GGTAGAGGAGACAGGTGTC-3'.
```

Four independent 3' RACE clones for chain 1 and three independent 3' RACE clones for chain 2 were isolated and sequenced in their entirety whereby the coding sequence of the postulated chains of Equ c s could be verified. DNA sequencing was performed using an Applied Biosystems 3130 Genetic Analyzer (Applied Biosystems, Foster City, Calif., USA). DNA and amino acid sequence analyses and calculations were performed using programs of the GCG Wisconsin Package (Accelrys, San Diego, Calif., USA).

Example 6: N-Terminal Sequencing and MALDI TOF Analysis Using the Postulated Sequences of Equ c s Chain 1 and Chain 2

Re-evaluation of the double amino acid sequence described in example 3 was performed using the postulated sequences of Equ c s. The double sequence can now be interpreted as DICPAV (residues 1-6 of SEQ ID NO: 3) and CPSFYAV (residues 1-7 of SEQ ID NO: 4) which are identical to the postulated N-terminal sequences of the mature chain 1 and chain 2 of the Equ c s protein.

Figure 5:
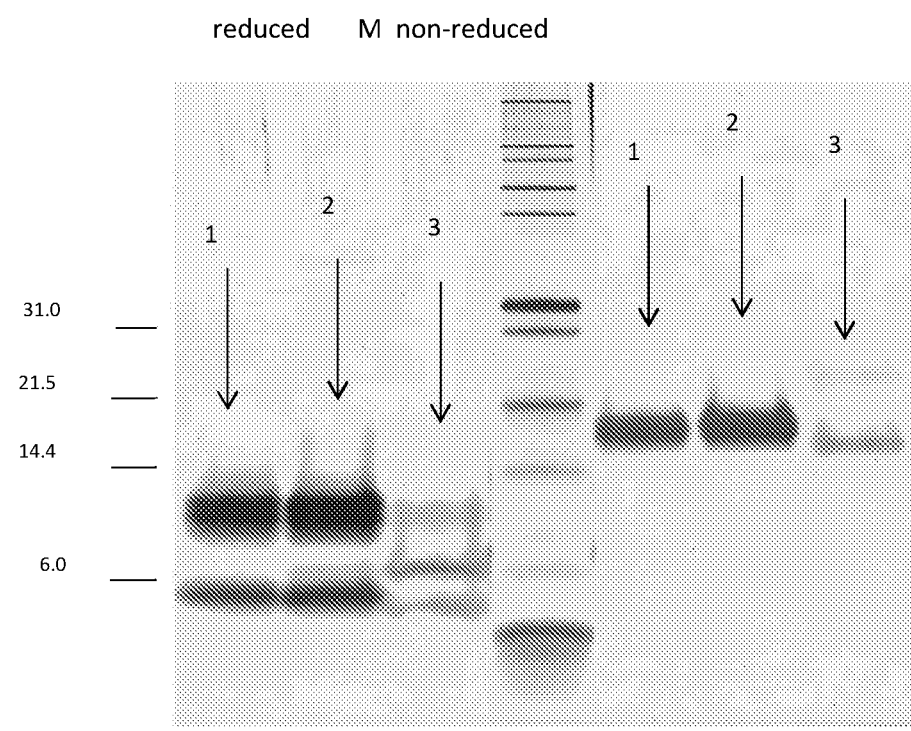

In gel digestion of the 5, 10 and 11 kDa bands of the reduced sample of peak 2 in FIG. 5 and the 18 kDa band of the non-reduced sample of the same peak was subjected to MALDI ToF peptide mass fingerprint (PMF) analysis, essentially as described in (Mattsson, Lundgren et al. 2009). In the 5 kDa band eight different peptides were detected having a mass that matched hypothetical trypsin cleaved peptides in the postulated Equ c s chain 1 sequence (table 7a). these peptides covered 89% of the postulated mature sequence including the N-terminal and C-terminal ends of the amino acid chain.

In the 11 kDa band two different peptides were detected that matched the mass of hypothetical trypsin cleaved peptides in the postulated Equ c s chain 2 sequence (table 7b). These peptides covered 32% of the postulated mature sequence including the N-terminal end of the amino acid chain. The reason that only a small part of the chain 2 sequence could be identified is that it contains an N-glycosylation and the fact that the trypsin cleavage sites are distributed so that either too large or too small peptides are produced. In the 18 kDa band, peptides from both chain 1 and chain 2 could be found.

Figure 8:
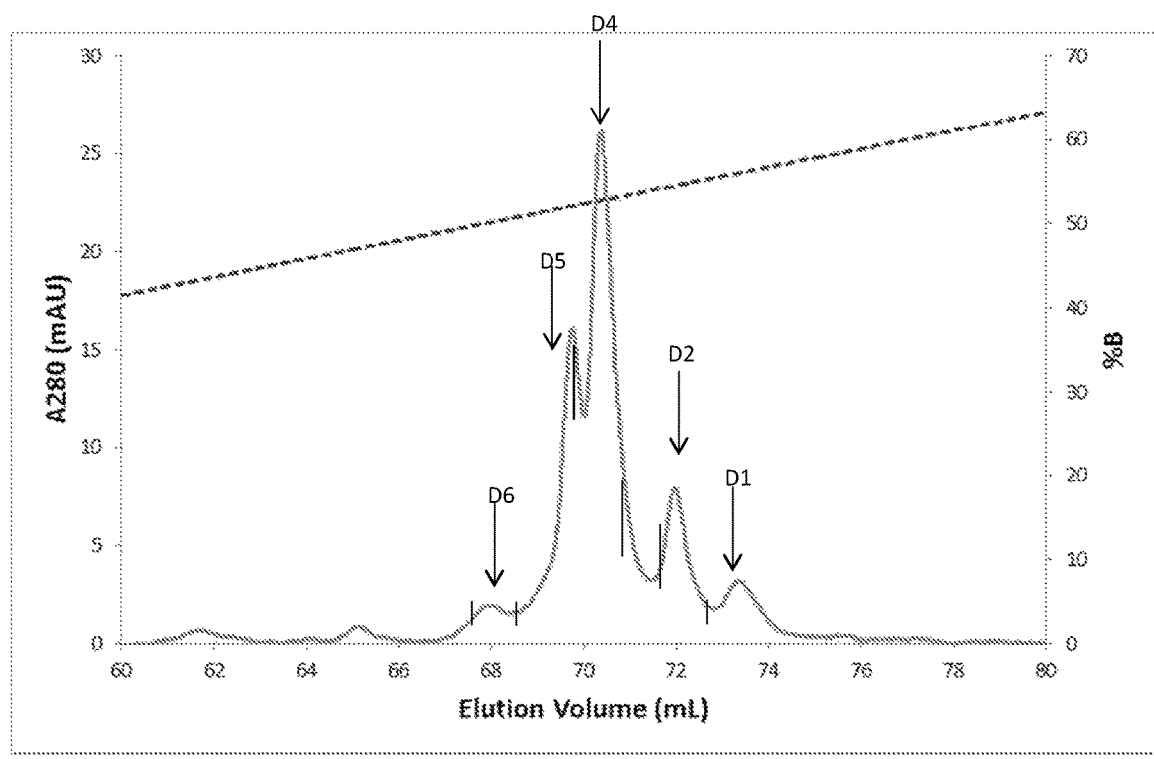

In order to increase the signal strength of these peptides to enable MS/MS analysis, two fractions from an RPC chromatography purification similar to that as described in example 2 but using a steeper gradient (FIG. 8) whereby the first two peaks do not become fully resolved were used. The fractions from these first two peaks (fraction D5 and D4) were reduced, alkylated with iodoacetamid and subjected to in solution digestion by trypsin. Using these samples, the whole amino acid sequence covered by the PMF analysis c from the 5 and 10 kDa band could be verified by MS/MS analysis to have sequences identical to the postulated fragments (table 8). A further analysis from this sample assumed semitrypsin cleavage sites (i.e. allowing that only one of the ends of each peptide was cleaved by trypsin) identified a large peptide fragment near the C terminal end of chain 2 (table 8).

The SDS-PAGE analysis (FIG. 5) and the mass spectrometric analysis above provides evidence that the 5 and 10 kDa amino acid chains can be identified as Equ c s, chain 1 and 2, respectively. In native non-reduced state, these amino acid chains are joined together by one or more disulfide bridges, thereby forming a heterodimeric protein. Thus, the analysis links together the sequence SEQ ID No 3, encoded by one gene, with SEQ ID No 4, encoded by a different gene, that together make up a previously unknown heterodimeric secretoglobin protein.

Example 7: Production and Immunological Characterization Recombinant Equ c s Cloning and Purification of Recombinant Equ c s A synthetic Equ c s single chain gene was designed by combining nucleotide sequences encoding the amino acid sequences of the 5 kDa and the 10 kDa subunits with a sequence encoding a linker peptide comprising 3× (Gly-Gly-Gly-Gly-Ser, residues 72-86 of SEQ ID NO: 5). The full-length synthetic gene was cloned into the NdeI and XhoI sites of vector pET23a(+) (Novagen, Madison, Wis., USA), adding a C-terminal hexahistidine tag to enable protein purification by immobilised metal ion affinity chromatography (IMAC).

The amino acid sequence for the whole recombinant protein (denominated rEqu c s ab) is

```
                                                       (SEQ ID NO: 5)
MDICPAVKED  VNIFLTGTPD  DYVKKVSQYQ  RNPVILANAE  KLKNCIDKKL  TAEDKENALS    60

VLEKIYSSDF  CGGGGSGGGG  SGGGGSCPSF  YAVLGVLSLG  SKTLLDTSLN  LVNATEPEKV   120

AMGKIQDCYN  EAGVITKISD  LIIMGTITTS  PECISHALST  LTTDVQEGIS  KLNPLGRLEH   180

HHHHH.                                                                  185
```

The nucleotide sequence was designed for optimal codon usage in *E. coli* (DNA2.0, Menlo Park, Calif., USA).

The nucleic acid sequence encoding the whole recombinant protein is

```
                                                       (SEQ ID NO: 6)
atggacattt  gccctgcggt  taaagaggac  gtcaacattt  ttctgaccgg  taccccagat    60
gattacgtca  aaaaagtgag  ccagtaccag  cgtaacccgg  ttattctggc  aaatgccgag   120
aaactgaaga  attgtatcga  caaaaagctg  acggctgagg  ataaggaaaa  cgccctgtct   180
gtcttggaga  agatttacag  cagcgacttc  tgtggtggcg  gtggcagcgg  tggtggtggt   240
tcgggcggtg  gcggcagctg  cccgtccttc  tatgcggtgc  tgggtgttct  gagcttaggt   300
agcaagaccc  tgttggacac  gagcctgaat  ttggtgaatg  cgactgaacc  ggagaaagtc   360
gcaatgggca  agatccaaga  ttgctataac  gaagcgggcg  ttatcaccaa  gatcagcgat   420
ctgatcatta  tgggtacgat  cacgaccagc  ccggaatgta  tctctcacgc  gctgtccacc   480
ctgaccaccg  acgtgcaaga  gggcattagc  aaactgaacc  cgctgggtcg  cctcgagcac   540
caccaccacc  accac.                                                       555
```

The nucleic acid sequence encoding chain 1 is

```
                                                       (SEQ ID NO: 9)
gacatttgcc  ctgcggttaa  agaggacgtc  aacattttc   tgaccggtac  cccagatgat    60
tacgtcaaaa  aagtgagcca  gtaccagcgt  aacccggtta  ttctggcaaa  tgccgagaaa   120
ctgaagaatt  gtatcgacaa  aaagctgacg  gctgaggata  aggaaaacgc  cctgtctgtc   180
ttggagaaga  tttacagcag  cgacttctgt                                       210
```

The nucleic acid encoding chain 2 is

```
                                                       (SEQ ID NO: 10)
tgcccgtcgt tttatgcagt cctgggtgtt ctgtctttgg gttctaaaac tttgctggac   60
acgagcctga atctggtgaa tgcaacggag cctgaaaagg tcgcgatggg caagattcag  120
gactgttaca acgaagcggg cgttattacc aagatcagcg acctgatcat tatgggcacg  180
atcaccacga gcccagagtg catcagccac gctttgtcca ccctgaccac cgatgtccaa  240
gagggcatta gcaagctgaa cccgctgggt cgc                              273
```

An alternative construct was designed having the 10 kDa subunit at the N-terminal end followed by the linker and the 5 kDa subunit, thereby connecting the two subunits in the other end of each amino acid chain. The amino acid sequence for the alternative recombinant protein (denominated rEqu c s ba) is

```
                                                        (SEQ ID NO: 7)
MCPSFYAVLG VLSLGSKTLL DTSLNLVNAT EPEKVAMGKI QDCYNEAGVI TKISDLIIMG   60

TITTSPECIS HALSTLTTDV QEGISKLNPL GRGGGGSGGG GSGGGGSDIC PAVKEDVNIF  120

LTGTPDDYVK KVSQYQRNPV ILANAEKLKN CIDKKLTAED KENALSVLEK IYSSDFCLEH  180

HHHHH                                                              185
``` and the nucleic acid sequence encoding the same protein is

```
                                                        (SEQ ID NO: 8)
atgtgcccgt cgtttatgc agtcctgggt gttctgtctt tgggttctaa aactttgctg   60
gacacgagcc tgaatctggt gaatgcaacg gagcctgaaa aggtcgcgat gggcaagatt  120
caggactgtt acaacgaagc gggcgttatt accaagatca gcgacctgat cattatgggc  180
acgatcacca cgagcccaga gtgcatcagc cacgctttgt ccaccctgac caccgatgtc  240
caagagggca ttagcaagct gaacccgctg gtcgcggtg gtggcggtag cggtggtggt  300
ggctccggtg gcggtggcag cgatatttgt ccggcggtga agaagatgt caacatcttc   360 ctgaccggta ccccggatga ttatgtgaaa aagttagcc ataccagcg taatccggtt   420 atcctggcca atgccgagaa actgaagaac tgcatcgaca aaaagctgac cgcagaggac  480
aaagaaaacg cgctgagcgt gctggagaag atttacagca gcgacttctg tctcgagcac  540
caccaccacc accac.                                                  555
```

The plasmid DNA constructs was transformed into E. coli strain BL21-AI (Invitrogen) and recombinant Equ c s single chain protein was produced using a 3-litre bioreactor (Belach Bioteknik, Skogås, Sweden).

The method of purification of recombinant Equ c s were almost identical for the two variants of the protein. Harvested cells was resuspended in 20 mM Tris-HCl pH 8.0 and lysed by passing the suspension through an Emulsiflex C5 homogenizor (Avestin, Ottawa, Ontario, Canada) at 10 000-15 000 kPa. After clarification by centrifugation and filtration, the supernatant was applied to a Chelating Sepharose FF column (GE Healthcare Life Sciences), charged with NiSO₄. Column washing was performed with 20 mM imidazole in 20 mM Tris-HCl pH 8.0, 0.15 M NaCl and the recombinant protein eluted in a linear 20-500 mM gradient of imidazole in the same buffer (FIG. 9a). Further purification of the recombinant protein was performed by AIEC in 20 mM Tris-HCl pH 8.0 using a Q Sepharose™ FF column (GE Healthcare Life Sciences). The protein was eluted using a linear 0-0.6 M NaCl gradient resulting in a double peak where the two peaks were pooled separately (FIG. 9b). The protein concentration of the preparations was determined from absorbance at 280 nm, using a calculated extinction coefficient of 0.34 per mg/mL.

Biochemical Characterisation of Recombinant Equ c s

Analytical gel filtration of peak 1 and peak 2 of rEqu c s ab demonstrated that peak 1 contained a mixture of dimeric and monomeric form of rEqu c s (FIG. 10 a) whereas peak 2 contained mostly aggregated material (FIG. 10 b). This result was also the case for the other recombinant form, rEqu c s ba (data not shown).

SDS PAGE analysis of single chain recombinant Equ c s demonstrated a single band at 19 kDa for reducing conditions and a slightly lower apparent molecular weight band at 16 kDa for nonreducing conditions (FIG. 10c). During non-reducing conditions higher molecular weight band predominantly at 39 kDa were also present, supposedly representing a dimeric form of the protein.

N-terminal sequence analysis of the first variant of rEqu c s (rEqu c s ab) resulted in a clear and unambiguous sequence readout with no deviation from expected sequence and where the initiator methionine was fully retained. In the preparation of the second variant, rEqu c s ba, the initiator methionine was retained in approximately half of the sample but the remainder of the preparation started at the second amino acid chain. In conclusion, both of the recombinant preparations contained intact rEqu c s.

Assessment of IgE Binding to Recombinant Equ c s

Each of peak 1 and 2 of the two forms of recombinant Equ c s was immobilised to experimental ImmunoCAP™ as described (Marknell DeWitt, Niederberger et al. 2002) and the IgE reactivity to the sera described in example 1 were used to assess the IgE reactivity of each of these preparations. According to table 9, all preparations had similar IgE reactivity to these sera which was also in accordance with the IgE reactivity of the purified fraction containing native protein (table 6, fraction 2).

Figure 4:
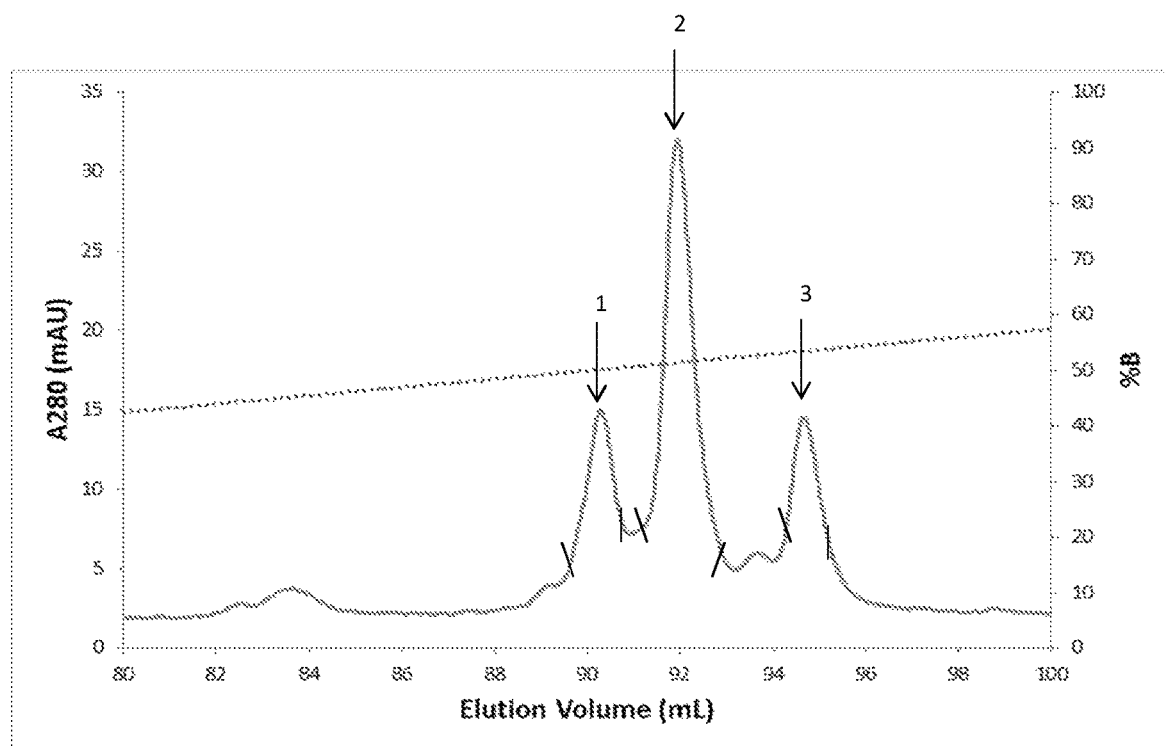

Further analysis of IgE reactivity using sera from 35 horse dander sensitized subjects was performed comparing recombinant Equ c s ab with the native purified protein fraction 2 from RPC (FIG. 4).

Figure 11:
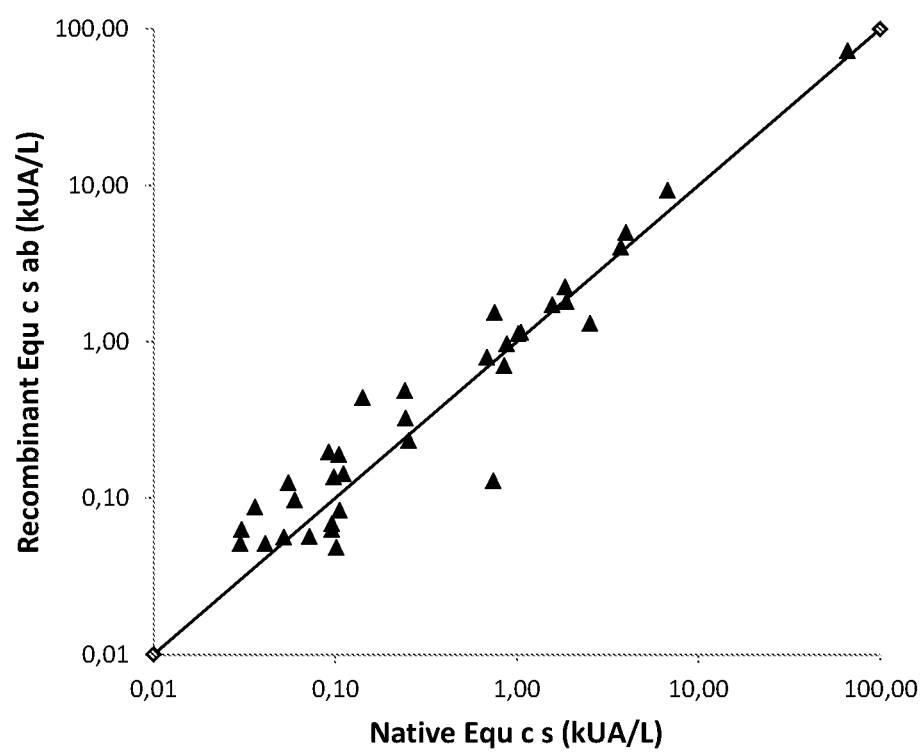

There was a good agreement (r=0.99) between IgE binding to purified native Equ c s and recombinant Equ c s (FIG. 11), demonstrating that the recombinant protein was immunologically active and structurally similar to the native protein. These data provide strong evidence that the amino acid sequence of the 5 kDa (SEQ ID NO: 3) and 10 kDa (SEQ ID NO: 4) subunits of Equ c s, as predicted from the genomic sequence information identified, are correct and represents the amino acid sequence of the purified horse dander allergen Equ c s.

Example 8: Assessment of IgE Binding Activity of nEqu c 1, nEqu c 2, nEqu c 3, nEqu c 4, Equ c 15k and Equ c s in a Cohort of Horse Allergic Patients Sera from 25 horse allergic subjects from Spain (n=20) and Sweden (n=5) were used in the study. All patients had a doctors' diagnosis of horse allergy with symptoms such as asthma, rhinoconjunctivitis and urticaria, and a positive skin prick test to horse dander extract. All samples and clinical data were collected under the approval of the local ethics committee at each center contributing to the biobank in which the samples and data had been deposited.

Figure 12:
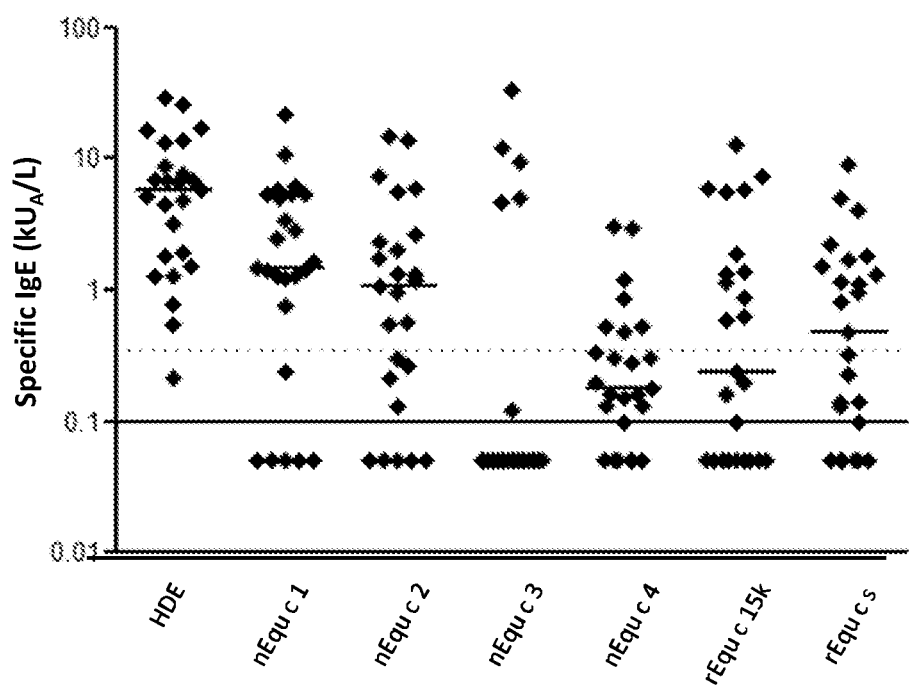

The levels of specific IgE antibodies to horse dander extract, nEqu c 1, nEqu c 2, nEqu c 3 and nEqu c 4, rEqu c 15k and rEqu c s ab among the 25 horse allergic subjects were determined using ImmunoCAP™ (FIG. 12, Table 10). In Table 10, all ImmunoCAP™ levels are displayed as $kU_A/L$ and the origin of each patient is indicated by ES (Spain) or SE (Sweden). Recorded allergic symptoms on exposure to horse are rhinitis (rhin), asthma (astm), urticaria (urt) or anaphylaxis (anaph).

Of the 25 sera tested, 13 (52%) showed an IgE response ≥0.35 $kU_A/L$ to rEqu c s whereas 12 (48%) had IgE reactivity to rEqu c 15k, 16 (64%) to nEqu c 2 and 19 (76%) to nEqu c 1. Both nEqu c 3 and nEqu c 4/5 appeared as minor allergens among the subjects studied, binding IgE ab from only 5 (20%) and 7 (28%) of the tested sera, respectively. In this study cohort none of the patients reacted exclusively to rEqu c s whereas four (16%) and two of the 25 sera reacted exclusively to Equ c 15k and Equ c 1, respectively. On average among all Equ c 15k-reactive sera, the concentration of IgE antibody to Equ c s amounted to 30% of that to horse dander.

The corresponding relative concentration of IgE antibody to nEqu c 1 was 52%, whereas for nEqu c 2, nEqu c 3, nEqu c 4/5 and Equ c 15k the relative concentrations were 35%, 69%, 9% and 37%, respectively, among sera specifically reactive to those allergens. Twenty-four of the 25 sera showed IgE antibody binding to horse dander extract. All of those sera showed binding to at least one of the five individual horse allergens tested. The sum of the IgE binding levels to the individual component matched or exceeded that to horse dander extract.

Example 9: Cross Reactivity Between Equ c s and Secretoglobin from Cat, the Major Cat Allergen Fel d 1

Figure 13:
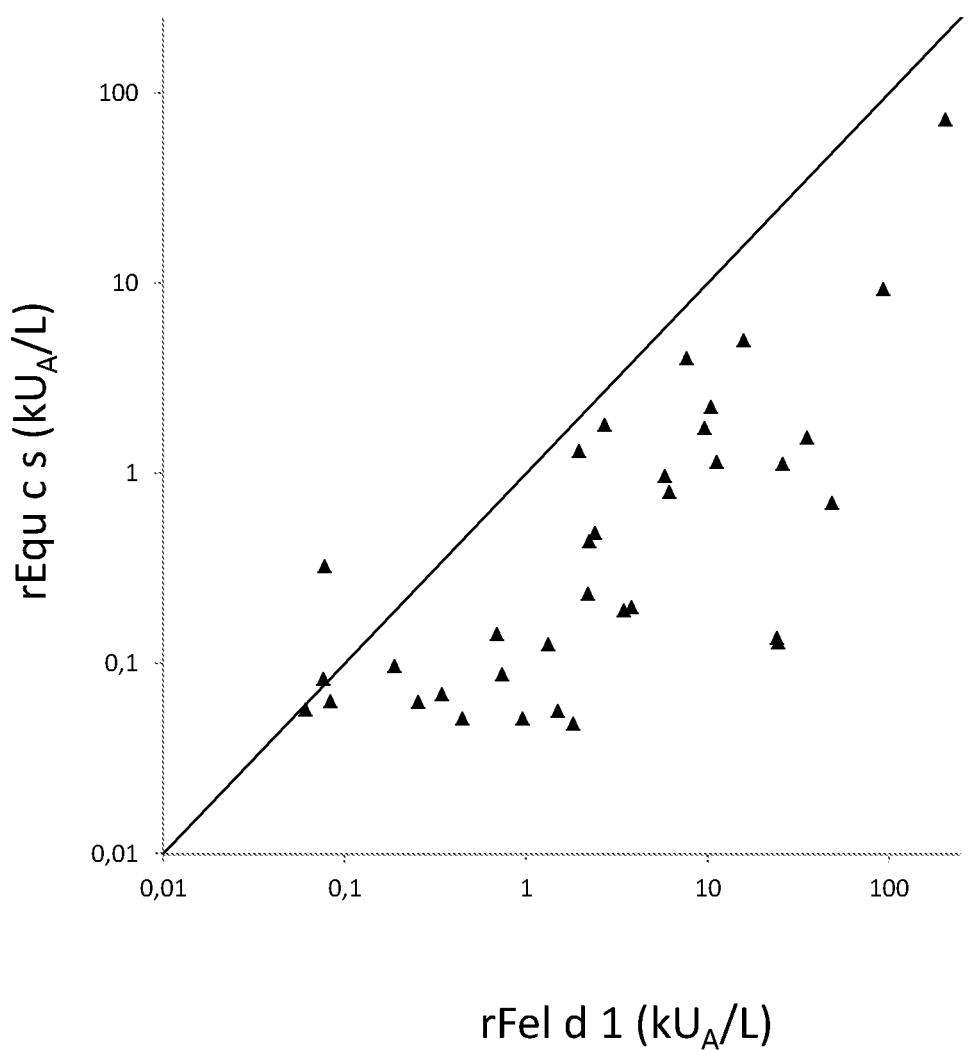

Since the unknown IgE reactivity that was the starting point of this study was inhibited by Fel d 1, the relationship between recombinant Equ c s and Fel d 1 was investigated. The levels of IgE binding to Fel d 1 was evaluated in sera of 35 horse dander sensitized subjects, including those 25 horse allergic patients described in Example 8. There was significant correlation (r=0.92) between the IgE levels to recombinant Equ c s and rFel d 1 (FIG. 13) and for almost all of the subjects the IgE reactivity to Fel d 1 was higher than that of Equ c s.

In order to further investigate the relationship between Equ c s and Fel d 1, the five sera used in example 1 were tested for cross-inhibition, using both horse dander extract, rFel d 1 and rEqu c s on solid phase as well as rEqu c 15k, rEqu c s and rFel d 1 as inhibitors at a final concentration of 100 µg/mL. As an inhibition control buffer, 0.1 M sodium phosphate buffer, pH 7.4, containing 0.3% human serum albumin, was used. Means of duplicate determinations of each inhibition were calculated and the fraction of inhibition was calculated as the fraction of the binding using inhibition control buffer that could be quenched with each inhibitor. In these selected sera, inhibition of binding to horse dander extract could only be achieved by Fel d 1 and Equ c s indicating that Equ c s indeed is the unknown protein in horse dander extract that is accountable for the binding of these sera (Table 11A). Binding to Fel d 1 immunoCAP can be inhibited by Fel d 1 itself but not by Equ c s (Table 11B) whereas binding to Equ c s could be inhibited by both Fel d 1 and Equ c s (Table 11C). This demonstrates that the IgE binding between Fel d 1 and Equ c s is indeed cross reactive as both the high extent of sequence homology between the two proteins (FIGS. 6C and 7C) and the high correlation of IgE binding to a population of horse dander sensitised sera suggests. Furthermore, the fact that Fel d 1 could inhibit binding to Equ c s solid phase but Equ c s could not inhibit binding to Fel d 1, as well as the fact that the IgE binding to Fel d 1 was always higher than to Equ c s in the population of horse dander sensitised sera suggested that these sera were originally sensitised to Fel d 1 and the binding to Equ c s was a result of cross reactivity.

Example 10: Assessment of IgE-Binding Properties of a Variant or Fragment (Analyte) of an Allergenic Protein The original allergenic protein, in this case Equ c s, is immobilized to a solid support. Serum samples from at least three representative human patients sensitized to the relevant species and showing IgE reactivity to the original allergenic protein from that species are incubated for 2 h at room temperature with the analyte at a final concentration of 100 µg/mL and, in parallel as negative controls, with buffer alone and the non-allergenic maltose binding protein (MBP) of *E. coli*. The samples are then analysed for IgE binding to solid supports carrying immobilized Equ c s to study whether preincubation with the variant or fragment of Equ c s specifically inhibits or significantly lowers IgE binding.

TABLE 1

IgE binding characteristics of sera utilised for detection of an unknown horse dander component.

| Serum | CDE kU$_A$/L | rFel d 1 kU$_A$/L | HDE kU$_A$/L | rEqu c 1 kU$_A$/L | nEqu c 2 kU$_A$/L | nEqu c 3 kU$_A$/L | nEqu c 4 kU$_A$/L | rEqu c 15K kU$_A$/L |
|---|---|---|---|---|---|---|---|---|
| A | >100 | >100 | 12.0 | 0.19 | 0.46 | 0.05 | 0.11 | 0.08 |
| B | 97.0 | 95.1 | 11.4 | 0.21 | 0.32 | 0.07 | 0.16 | 0.08 |
| C | 87.9 | >100 | 10.9 | 0.13 | 0.21 | 0.03 | 0.08 | 0.06 |
| D | 61.9 | 69.0 | 7.36 | 0.11 | 0.16 | 0.04 | 0.09 | 0.06 |
| E | 67.6 | 61.0 | 6.28 | 0.02 | 0.04 | 0.14 | 0.02 | 0.00 |

CDE—cat dander extract
HDE—horse dander extract

TABLE 2

Inhibition of IgE binding to a) cat dander extract and b) horse dander extract, using the inhibitors Equ c 15k, Fel d 1 and Fel d 7.

| Serum | Inhibitor | Concentration (kUA/L) | Inhibition (%) |
|---|---|---|---|
| \multicolumn{4}{l}{a) binding to cat dander extract solid phase} | | | |
| A | buffer | 73.3 | 0 |
|   | Equ c 15k | 74.6 | -2 |
|   | Fel d 1 | 13.5 | 82 |
|   | Fel d 7 | 76.2 | -4 |
| B | buffer | 59.7 | 0 |
|   | Equ c 15k | 56.4 | 6 |
|   | Fel d 1 | 8.5 | 86 |
|   | Fel d 7 | 58.7 | 2 |
| C | buffer | 55.9 | 0 |
|   | Equ c 15k | 57.2 | -2 |
|   | Fel d 1 | 9.06 | 84 |
|   | Fel d 7 | 57.6 | -3 |
| D | buffer | 39.1 | 0 |
|   | Equ c 15k | 39.1 | 0 |
|   | Fel d 1 | 6.17 | 84 |
|   | Fel d 7 | 37.7 | 4 |
| E | buffer | 53.6 | 0 |
|   | Equ c 15k | 51.2 | 4 |
|   | Fel d 1 | 19.0 | 65 |
|   | Fel d 7 | 56.7 | -6 |
| \multicolumn{4}{l}{b) binding to horse dander extract solid phase} | | | |
| A | buffer | 7.46 | 0 |
|   | Equ c 15k | 7.87 | -5 |
|   | Fel d 1 | 0.12 | 98 |
|   | Fel d 7 | 7.99 | -7 |
| B | buffer | 6.42 | 0 |
|   | Equ c 15k | 6.57 | -2 |
|   | Fel d 1 | 0.22 | 97 |
|   | Fel d 7 | 6.84 | -6 |
| C | buffer | 6.27 | 0 |
|   | Equ c 15k | 5.97 | 5 |
|   | Fel d 1 | 0.11 | 98 |
|   | Fel d 7 | 6.09 | 3 |
| D | buffer | 4.20 | 0 |
|   | Equ c 15k | 4.04 | 4 |
|   | Fel d 1 | 0.10 | 98 |
|   | Fel d 7 | 4.42 | -5 |
| E | buffer | 4.64 | 0 |
|   | Equ c 15k | 4.56 | 2 |
|   | Fel d 1 | 0.06 | 99 |
|   | Fel d 7 | 4.70 | -1 |

TABLE 3

IgE binding of detector sera to immobilised fractions from SEC chromatography of horse dander extract

| | Fraction | | | | | |
|---|---|---|---|---|---|---|
| Serum | 18 kU$_A$/L | 22 kU$_A$/L | 26 kU$_A$/L | 30 kU$_A$/L | 34 kU$_A$/L | 38 kU$_A$/L |
| A | 18.9 | 16.4 | 18.3 | 10.1 | 4.01 | 1.78 |
| B | 12.4 | 11.5 | 11.8 | 7.02 | 3.04 | 1.53 |
| C | 15.2 | 12.3 | 12.2 | 7.25 | 3.02 | 1.46 |
| D | 10.7 | 8.79 | 8.44 | 5.40 | 2.22 | 1.02 |
| E | 11.0 | 9.31 | 9.24 | 6.45 | 2.49 | 0.77 |

TABLE 4

IgE binding of detector sera to immobilised fractions from HIC chromatography of an enriched fraction from horse dander extract

| | Fraction | | | | | | |
|---|---|---|---|---|---|---|---|
| Sera | 8 kU$_A$/L | 17 kU$_A$/L | 23 kU$_A$/L | 36 kU$_A$/L | 39 kU$_A$/L | 42 kU$_A$/L | 60 kU$_A$/L |
| A | 0.21 | 0.25 | 0.44 | 2.67 | 3.99 | 11.9 | 22.9 |
| B | 0.29 | 0.65 | 0.55 | 2.69 | 3.15 | 9.43 | 16.8 |
| C | 0.17 | 0.22 | 0.30 | 2.03 | 3.25 | 9.98 | 18.0 |
| D | 0.17 | 0.19 | 0.26 | 1.59 | 2.27 | 6.62 | 11.4 |
| E | 0.06 | 0.16 | 0.19 | 1.15 | 2.20 | 8.32 | 13.9 |

TABLE 5

IgE binding of detector sera to immobilised fractions from anion exchange chromatography of an enriched fraction from horse dander extract.

a) Immobilised fractions at dilution 1:4

| | Fraction | | | | | | |
|---|---|---|---|---|---|---|---|
| Sera | B3 kU$_A$/L | B2 kU$_A$/L | C1 kU$_A$/L | C2 kU$_A$/L | C5 kU$_A$/L | C8 kU$_A$/L | D9 kU$_A$/L |
| A | 25.7 | 25.5 | 23.5 | 23.3 | 20.3 | 20.5 | 5.2 |
| B | 18.1 | 17.9 | 17.9 | 16.9 | 16.2 | 16.3 | 4.0 |
| C | 17.1 | 16.8 | 16.8 | 16.7 | 17.1 | 16.2 | 3.8 |
| D | 11.6 | 11.7 | 11.7 | 11.2 | 11.4 | 10.3 | 2.6 |
| E | 14.9 | 14.4 | 14.7 | 13.9 | 14.5 | 12.1 | 2.0 |

TABLE 5-continued

IgE binding of detector sera to immobilised fractions from anion exchange chromatography of an enriched fraction from horse dander extract.

b) Immobilised pools at dilution 1:20

| Sera | Fraction | | |
|---|---|---|---|
| | B4-B1 $kU_A/L$ | C1-C4 $kU_A/L$ | C5-C11 $kU_A/L$ |
| A | 10.71 | 9.00 | 6.50 |
| B | 8.92 | 7.67 | 5.07 |
| C | 8.46 | 6.72 | 4.97 |
| D | 5.44 | 4.48 | 3.26 |
| E | 5.74 | 4.46 | 3.00 |

TABLE 6

IgE binding of detector sera to immobilised fractions from RPC chromatography of an enriched fraction from horse dander extract.

| Sera | Fraction | | |
|---|---|---|---|
| | 1 $kU_A/L$ | 2 $kU_A/L$ | 3 $kU_A/L$ |
| A | 17.8 | 21.1 | 5.52 |
| B | 13.2 | 15.1 | 4.41 |
| C | 13.5 | 15.2 | 4.14 |
| D | 9.68 | 11.0 | 2.97 |
| E | 8.10 | 9.99 | 1.92 |

TABLE 7

Peptide fragments matching the theoretical masses of trypsin cleaved Equ c s from in gel digestion of a) 5 kDa b and b) 10 kDa band of reduced sample and c) 18 kDa band of non-reduced sample.

| m/z measured | m/z theoretical | Equ c s chain | range | peptide | SEQ ID NO: |
|---|---|---|---|---|---|
| a) | | | | | |
| 2609.29 | 2609.28 | 1 | 23-45 | -.DICPAVKEDVNIFLTGTPDDYVK.K | 17 |
| 1825.85 | 1825.88 | 1 | 30-45 | K.EDVNIFLTGTPDDYVK.K | 18 |
| 1953.97 | 1953.98 | 1 | 30-46 | K.EDVNIFLTGTPDDYVKK.V | 19 |
| 908.50 | 908.49 | 1 | 46-52 | K.KVSQYQR.N | 20 |
| 780.39 | 780.39 | 1 | 47-52 | K.VSQYQR.N | 21 |
| 1068.59 | 1068.6 | 1 | 53-62 | R.NPVILANAEK.I | 22 |
| 1659.84 | 1659.88 | 1 | 71-85 | K.LTAEDKENALSVLEK.I | 23 |
| 891.39 | 891.35 | 1 | 86-92 | K.IYSSDFC.- | 24 |
| b) | | | | | |
| 1697.84 | 1697.89 | 2 | 24-39 | -CPSFYAVLGVLSLGSK.T | 25 |
| 1510.67 | 1510.72 | 2 | 62-74 | K.IQDCYNEAGVITK.I | 26 |
| c) | | | | | |
| 2609.31 | 2609.28 | 1 | 23-45 | -.DICPAVKEDVNIFLTGTPDDYVK.K | 27 |
| 1825.86 | 1825.88 | 1 | 30-45 | K.EDVNIFLTGTPDDYVK.K | 28 |
| 1953.93 | 1953.98 | 1 | 30-46 | K.EDVNIFLTGTPDDYVKK.V | 29 |
| 908.46 | 908.49 | 1 | 46-52 | K.KVSQYQR.N | 30 |
| 1068.56 | 1068.6 | 1 | 53-62 | R.NPVILANAEK.I | 31 |
| 1659.84 | 1659.88 | 1 | 71-85 | K.LTAEDKENALSVLEK.I | 32 |
| 1510.69 | 1510.72 | 2 | 62-74 | K.IQDCYNEAGVITK.I | 33 |

TABLE 8

Peptides identified by MS/MS from in-solution digested fraction from RPC.

| m/z measured | m/z theoretical | MS/MS score | Equ c s chain | range | peptide | SEQ ID NO: |
|---|---|---|---|---|---|---|
| 802.34 | 802.41 | 22.2 | 1 | 23-29 | -.DICPAVK.E | 34 |
| 1825.96 | 1825.88 | 88.0 | 1 | 30-45 | K.EDVNIFLTGTPDDYVK.K | 35 |
| 908.46 | 908.49 | 55.3 | 1 | 46-52 | K.KVSQYQR.N | 36 |
| 780.34 | 780.39 | 25.9 | 1 | 47-52 | K.VSQYQR.N | 37 |
| 1068.58 | 1068.6 | 75.9 | 1 | 53-62 | R.NPVILANAEK.I | 38 |
| 1659.89 | 1659.88 | 82.4 | 1 | 71-85 | K.LTAEDKENALSVLEK.I | 39 |
| 891.31 | 891.35 | 14.8 | 1 | 86-92 | K.IYSSDFC.- | 40 |
| 1510.75 | 1510.72 | 127.2 | 2 | 62-74 | K.IQDCYNEAGVITK.I | 41 |
| 1697.90 | 1697.89 | 128.3 | 2 | 24-39 | -.CPSFYAVLGVLSLGSK.T | 42 |
| 2573.50 | 2573.32 | 53.4 | 2 | 75-98 | K.ISDLIIMGTITTSPECISHALSTL.T* | 43 |

*Peptide identified by semitrypsin cleavage of protein.

TABLE 9

IgE reactivity of rEqu s c preparations

| Sera | peak 1 rEqu c s ba kU$_A$/l | peak 2 rEqu c s ba kU$_A$/l | peak 1 rEqu c s ab kU$_A$/l | peak 2 rEqu c s ab kU$_A$/l |
|---|---|---|---|---|
| A | 24.87 | 23.09 | 23.40 | 23.12 |
| B | 15.70 | 15.02 | 15.61 | 15.23 |
| C | 15.15 | 15.34 | 16.77 | 15.57 |
| D | 15.41 | 15.59 | 16.10 | 15.50 |
| E | 13.16 | 12.99 | 13.05 | 13.23 |

TABLE 10

IgE reactivity of 25 horse allergic patients

| Patient no | symptoms | Country | e3 | nEqu c 1 | nEqu c 2 | nEqu c 3 | nEqu c 4 | rEqu c 15k | rEqu c s |
|---|---|---|---|---|---|---|---|---|---|
| 1 | Rhin | SE | 1.55 | 0.06 | 0.21 | 0.12 | 0.30 | 1.31 | 0.14 |
| 2 | Rhin, astm | SE | 1.28 | 1.24 | 0.56 | 0.00 | 0.16 | 0.03 | 0.48 |
| 3 | Rhin | ES | 4.79 | 1.42 | 0.13 | 0.00 | 0.04 | 1.89 | 0.05 |
| 4 | Rhin, astm | ES | 5.87 | 4.96 | 2.32 | 0.07 | 0.53 | 0.16 | 1.14 |
| 5 | Rhin, astm | ES | 1.79 | 1.28 | 0.26 | 0.01 | 0.15 | 0.04 | 1.12 |
| 6 | Rhin, astm | ES | 8.74 | 5.41 | 5.56 | 0.00 | 0.34 | 0.02 | 0.80 |
| 7 | Rhin, astm | ES | 0.21 | 0.00 | 0.02 | 0.00 | 0.02 | 0.20 | 0.06 |
| 8 | Rhin, astm | ES | 4.55 | 1.41 | 2.02 | 0.00 | 0.53 | 0.86 | 0.10 |
| 9 | Rhin | ES | 0.55 | 0.00 | 0.01 | 0.00 | 0.02 | 0.63 | 0.06 |
| 10 | astm, urt, a | ES | 17.31 | 6.20 | 2.67 | 11.90 | 3.11 | 6.07 | 0.08 |
| 11 | Rhin | ES | 16.62 | 1.30 | 15.15 | 5.04 | 0.86 | 0.10 | 1.72 |
| 12 | Rhin, urt | ES | 13.49 | 2.91 | 1.19 | 0.03 | 0.30 | 12.96 | 1.31 |
| 13 | hin, astm, u | SE | 26.19 | 11.04 | 7.48 | 0.05 | 2.94 | 5.68 | 1.80 |
| 14 | Rhin | SE | 6.58 | 3.42 | 1.08 | 0.01 | 0.48 | 1.16 | 2.23 |
| 15 | Rhin, astm | SE | 7.01 | 0.03 | 0.04 | 0.00 | 0.20 | 7.45 | 0.13 |
| 16 | Rhin | ES | 6.78 | 5.77 | 0.95 | 9.43 | 0.28 | 0.02 | 0.97 |
| 17 | Rhin | ES | 28.73 | 21.92 | 5.89 | 33.75 | 1.19 | 0.24 | 9.25 |
| 18 | Rhin, urt | ES | 13.81 | 5.44 | 14.10 | 0.05 | 0.13 | 0.07 | 0.14 |
| 19 | Rhin, astm | ES | 5.18 | 0.06 | 0.08 | 0.06 | 0.18 | 5.81 | 1.54 |
| 20 | Rhin, astm | ES | 0.78 | 0.76 | 0.09 | 0.01 | 0.02 | 0.02 | 0.06 |
| 21 | Rhin, astm | ES | 1.96 | 1.63 | 0.58 | 0.01 | 0.16 | 0.04 | 0.32 |
| 22 | Rhin, urt | ES | 1.28 | 0.24 | 1.75 | 0.01 | 0.02 | 0.06 | 0.23 |
| 23 | Rhin, astm | ES | 6.94 | 2.49 | 0.30 | 0.00 | 0.10 | 1.36 | 4.02 |
| 24 | Rhin, astm | ES | 3.18 | 1.46 | 1.31 | 0.00 | 0.13 | 0.60 | 0.05 |
| 25 | Rhin | ES | 7.78 | 5.46 | 1.32 | 4.61 | 0.08 | 0.03 | 4.99 |

TABLE 11

Inhibition of IgE binding to a) horse dander extract,
b) rFel d 1 and c) rEqu c s solid phase, using the
inhibitors Equ c 15k, Equ c s and Fel d 1.

| Serum | Inhibitor | Concentration (kUA/L) | Inhibition (%) |
|---|---|---|---|
| a) binding to horse dander extract solid phase | | | |
| A | buffer | 6.71 | 0 |
|   | Equ c 15k | 7.40 | −10 |
|   | Equ c s | 0.27 | 96 |
|   | Fel d 1 | 0.13 | 98 |
| B | buffer | 5.03 | 0 |
|   | Equ c 15k | 5.10 | −2 |
|   | Equ c s | 0.33 | 93 |
|   | Fel d 1 | 0.20 | 96 |
| C | buffer | 5.49 | 0 |
|   | Equ c 15k | 5.50 | 0 |
|   | Equ c s | 0.25 | 96 |
|   | Fel d 1 | 0.12 | 98 |
| D | buffer | 5.01 | 0 |
|   | Equ c 15k | 5.32 | −6 |
|   | Equ c s | 0.22 | 96 |
|   | Fel d 1 | 0.13 | 97 |
| E | buffer | 3.70 | 0 |
|   | Equ c 15k | 4.06 | −10 |
|   | Equ c s | 0.09 | 98 |
|   | Fel d 1 | 0.06 | 98 |
| b) binding to rFel d 1 solid phase | | | |
| A | buffer | 54.97 | 0 |
|   | Equ c 15k | 57.45 | −5 |
|   | Equ c s | 58.70 | −7 |
|   | Fel d 1 | 5.22 | 91 |
| B | buffer | 42.07 | 0 |
|   | Equ c 15k | 43.80 | −4 |
|   | Equ c s | 43.20 | −3 |
|   | Fel d 1 | 3.87 | 91 |
| C | buffer | 47.30 | 0 |
|   | Equ c 15k | 49.98 | −6 |
|   | Equ c s | 48.35 | −2 |
|   | Fel d 1 | 4.01 | 92 |
| D | buffer | 44.15 | 0 |
|   | Equ c 15k | 45.25 | −2 |
|   | Equ c s | 41.90 | 5 |
|   | Fel d 1 | 3.85 | 91 |
| E | buffer | 32.38 | 0 |
|   | Equ c 15k | 33.32 | −3 |
|   | Equ c s | 29.99 | 7 |
|   | Fel d 1 | 2.02 | 94 |
| c) binding to rEqu c s solid phase | | | |
| A | buffer | 13.39 | 0 |
|   | Equ c 15k | 11.73 | 12 |
|   | Equ c s | 5.30 | 60 |
|   | Fel d 1 | 0.59 | 96 |
| B | buffer | 9.08 | 0 |
|   | Equ c 15k | 8.63 | 5 |
|   | Equ c s | 3.47 | 62 |
|   | Fel d 1 | 0.45 | 95 |
| C | buffer | 10.05 | 0 |
|   | Equ c 15k | 9.37 | 7 |
|   | Equ c s | 3.82 | 62 |
|   | Fel d 1 | 0.40 | 96 |
| D | buffer | 9.22 | 0 |
|   | Equ c 15k | 8.44 | 8 |
|   | Equ c s | 3.76 | 59 |
|   | Fel d 1 | 0.40 | 96 |
| E | buffer | 6.60 | 0 |
|   | Equ c 15k | 6.33 | 4 |
|   | Equ c s | 1.59 | 76 |
|   | Fel d 1 | 0.24 | 96 |

REFERENCES

Akdis, C. A. (2006). "Allergy and hypersensitivity: mechanisms of allergic disease." *Curr Opin Immunol* 18(6): 718-726.

Akdis, M. and C. A. Akdis (2007). "Mechanisms of allergen-specific immunotherapy." *J Allergy Clin Immunol* 119(4): 780-791.

Asarnoj, A., R. Moverare, et al. (2010). "IgE to peanut allergen components: relation to peanut symptoms and pollen sensitization in 8-year-olds." *Allergy*.

Asarnoj, A., C. Nilsson, et al. (2012). "Peanut component Ara h 8 sensitization and tolerance to peanut." *J Allergy Clin Immunol* 130(2): 468-472.

Breiteneder, H., K. Hoffmann-Sommergruber, et al. (1997). "Recombinant allergens; basic and practical considerations." *Arbeiten aus dem Paul Ehrlich Institut-Bundesamt fur Sera and Impfstoffe-Zu Frankfurt Am* (91): 80-86.

Cabañas, R., M. C. López-Serrano, et al. (2000). "Importance of albumin in cross-reactivity among cat, dog and horse allergens." *Journal of Investigational Allergology and Clinical Immunology* 10(2): 71-77.

Canonica, G. W., I. J. Ansotegui, et al. (2013). "A WAO-ARIA-GA2LEN consensus document on molecular-based allergy diagnostics." *World Allergy Organ J* 6(1): 17.

Caubet, J. C., R. Bencharitiwong, et al. (2012). "Significance of ovomucoid- and ovalbumin-specific IgE/IgG(4) ratios in egg allergy." *J Allergy Clin Immunol* 129(3): 739-747.

Codreanu, F., O. Collignon, et al. (2011). "A novel immunoassay using recombinant allergens simplifies peanut allergy diagnosis." *Int Arch Allergy Immunol* 154(3): 216-226.

Cromwell, O., H. Fiebig, et al. (2006). "Strategies for recombinant allergen vaccines and fruitful results from first clinical studies." *Immunol Allergy Clin North Am* 26(2): 261-281, vii.

Custovic, A., L. Soderstrom, et al. (2011). "Allergen-specific IgG antibody levels modify the relationship between allergen-specific IgE and wheezing in childhood." *J Allergy Clin Immunol* 127(6): 1480-1485.

Dandeu, J. P., J. Rabillon, et al. (1993). "Hydrophobic Interaction Chromatography for Isolation and Purification of Equ.C1, the Horse Major Allergen." *Journal of Chromatography—Biomedical Applications* 621(1): 23-31.

Du Toit, G., G. Roberts, et al. (2015). "Randomized trial of peanut consumption in infants at risk for peanut allergy." *N Engl J Med* 372(9): 803-813.

Ebisawa, M., R. Moverare, et al. (2012). "Measurement of Ara h 1-, 2-, and 3-specific IgE antibodies is useful in diagnosis of peanut allergy in Japanese children." *Pediatr Allergy Immunol* 23(6): 573-581.

Ebisawa, M., R. Shibata, et al. (2012). "Clinical utility of IgE antibodies to omega-5 gliadin in the diagnosis of wheat allergy: a pediatric multicenter challenge study." *Int Arch Allergy Immunol* 158(1): 71-76.

Goubran Botros, H., C. Gregoire, et al. (1996). "Cross-antigenicity of horse serum albumin with dog and cat albumins: study of three short peptides with significant inhibitory activity towards specific human IgE and IgG antibodies." *Immunology* 88(3): 340-347.

Goubran Botros, H., P. Poncet, et al. (2001). "Biochemical characterization and surfactant properties of horse allergens." *Eur J Biochem* 268(10): 3126-3136.

Goubran Botros, H., J. Rabillon, et al. (1998). "Thiophilic adsorption chromatography: purification of Equ c2 and Equ c3, two horse allergens from horse sweat." *Journal of Chromatography. B, Biomedical Sciences & Applications* 710(1-2): 57-65.

Gregoire, C., I. Rosinski-Chupin, et al. (1996). "cDNA cloning and sequencing reveal the major horse allergen Equ c1 to be a glycoprotein member of the lipocalin superfamily." *Journal of Biological Chemistry* 271(51): 32951-32959.

Gronlund, H., T. Saarne, et al. (2009). "The Major Cat Allergen, Fel d 1, in Diagnosis and Therapy." *Int Arch Allergy Immunol* 151(4): 265-274.

Hiller, R., S. Laffer, et al. (2002). "Microarrayed allergen molecules: diagnostic gatekeepers for allergy treatment." *FASEB Journal* 16(3): 414-416.

Jutel, M., L. Jaeger, et al. (2005). "Allergen-specific immunotherapy with recombinant grass pollen allergens." *J Allergy Clin Immunol* 116(3): 608-613.

Kim, J. L., L. Elfman, et al. (2005). "Current asthma and respiratory symptoms among pupils in relation to dietary factors and allergens in the school environment." *Indoor Air* 15(3): 170-182.

Laukaitis, C. and R. Karn (2005). "evolution of the secretoglobins: a genomic and proteomic view." *biol J Linnean Soc* 84: 493-501.

Liccardi, G., G. D'Amato, et al. (2011). "Sensitization to Horse Allergens in Italy: A Multicentre Study in Urban Atopic Subjects without Occupational Exposure." *Int Arch Allergy Immunol* 155(4): 412-417.

Marknell DeWitt, Å., V. Niederberger, et al. (2002). "Molecular and immunological characterization of a novel timothy grass (*Phleum pratense*) pollen allergen, Phl p 11." *Clinical & Experimental Allergy* 32(9): 1329-1340.

Masthoff, L. J., L. Mattsson, et al. (2013). "Sensitization to Cor a 9 and Cor a 14 is highly specific for a hazelnut allergy with objective symptoms in Dutch children and adults." *J Allergy Clin Immunol* 132(2): 393-399.

Matsuo, H., J. Dahlstrom, et al. (2008). "Sensitivity and specificity of recombinant omega-5 gliadin-specific IgE measurement for the diagnosis of wheat-dependent exercise-induced anaphylaxis." *Allergy* 63(2): 233-236.

Mattsson, L., T. Lundgren, et al. (2009). "Prostatic kallikrein: A new major dog allergen." *J Allergy Clin Immunol* 123(2): 362-368.

McDonald, R. E., R. I. Fleming, et al. (2009). "Latherin: a surfactant protein of horse sweat and saliva." *PLoS One* 4(5): e5726.

Müller, U., P. Schmid-Grendelmeier, et al. (2012). "IgE to recombinant allergens Api m 1, Ves v 1, and Ves v 5 distinguish double sensitization from crossreaction in venom allergy." *Allergy* 67(8): 1069-1073.

Nicolaou, N., M. Poorafshar, et al. (2010). "Allergy or tolerance in children sensitized to peanut: prevalence and differentiation using component-resolved diagnostics." *J Allergy Clin Immunol* 125(1): 191-197 e191-113.

Ronmark, E., M. Perzanowski, et al. (2003). "Different sensitization profile for asthma, rhinitis, and eczema among 7-8-year-old children: report from the Obstructive Lung Disease in Northern Sweden studies." *Pediatr Allergy Immunol* 14(2): 91-99.

Saarelainen, S., M. Rytkonen-Nissinen, et al. (2008) "Animal-derived lipocalin allergens exhibit immunoglobulin E cross-reactivity." *Clin Exp Allergy* 38(2): 374-381.

Saarne, T., L. Kaiser, et al. (2005). "Rational design of hypoallergens applied to the major cat allergen Fel d 1." *Clin Exp Allergy* 35(5): 657-663.

Smith, W., A. J. Butler, et al. (2004). "Fel d 4, a cat lipocalin allergen." *Clinical & Experimental Allergy* 34(11): 1732-1738.

Spitzauer, S., C. Schweiger, et al. (1993). "Characterisation of dog allergens by means of immunoblotting." *International Archives of Allergy and Immunology* 100: 60-67.

Stumvoll, S., K. Westritschnig, et al. (2003). "Identification of cross-reactive and genuine *Parietaria judaica* pollen allergens." *Journal of Allergy and Clinical Immunology* 111(5): 974-979.

Tutluoglu, B., S. Atis, et al. (2002). "Sensitization to horse hair, symptoms and lung function in grooms." *Clin Exp Allergy* 32(8): 1170-1173.

Uermosi, C., R. R. Beerli, et al. (2010). "Mechanisms of allergen-specific desensitization." *J Allergy Clin Immunol* 126(2): 375-383.

Uermosi, C., F. Zabel, et al. (2014). "IgG-mediated down-regulation of IgE bound to mast cells: a potential novel mechanism of allergen-specific desensitization." *Allergy* 69(3): 338-347.

Wainstein, B. K., A. Yee, et al. (2007). "Combining skin prick, immediate skin application and specific-IgE testing in the diagnosis of peanut allergy in children." *Pediatr Allergy Immunol* 18(3): 231-239.

Valenta, R., J. Lidholm, et al. (1999). "The recombinant allergen-based concept of component-resolved diagnostics and immunotherapy (CRD and CRIT)." *Clinical and Experimental Allergy* 29(7): 896-904.

Valenta, R. and V. Niederberger (2007). "Recombinant allergens for immunotherapy." *J Allergy Clin Immunol* 119(4): 826-830.

The invention claimed is:

1. A method for detecting antibody, comprising the steps of
   contacting an immunoglobulin-containing body fluid sample from a patient suspected of having Type 1 allergy with an isolated heterodimeric protein having a first peptide chain and a second peptide chain together having an overall sequence identity of at least 90% with the combined sequences of SEQ ID NO: 3 and SEQ ID NO: 4, the isolated heterodimeric protein comprising at least one IgE antibody epitope of a heterodimeric protein having a first peptide chain having the sequence according to SEQ ID NO: 3 and a second peptide chain having the sequence according to SEQ ID NO: 4; and
   detecting the presence in the sample of antibodies specifically binding to said isolated heterodimeric protein.

2. A method according to claim 1, which comprises detecting the presence in the sample of IgE and/or IgG antibodies specifically binding to said isolated heterodimeric protein.

3. The method according to claim 1, further comprising the steps of
   contacting the immunoglobulin-containing body fluid sample from the patient suspected of having Type 1 allergy with at least one further purified allergen component from horse; and
   detecting the presence, in the sample, of IgE antibodies specifically binding to said purified allergen component from horse.

4. The method according to claim 3, wherein the further purified allergen component from horse is selected from the group consisting of native and recombinant Equ c 1, Equ c 2, Equ c 3, Equ c 4/5, and Equ c 15k.

5. A method for detecting antibody, comprising the steps of
   contacting an immunoglobulin-containing body fluid sample from a patient suspected of having Type 1 allergy with a single chain protein having an overall sequence identity of at least 90% with the combined amino acid sequences of SEQ ID NO: 3 and SEQ ID NO: 4, the single chain protein comprising at least one IgE antibody epitope of a heterodimeric protein having a first peptide chain having the sequence according to SEQ ID NO: 3 and a second peptide chain having the sequence according to SEQ ID NO: 4; and
   detecting the presence in the sample of antibodies specifically binding to said single chain protein.

6. The method of claim 1, wherein the isolated heterodimeric protein has a first peptide chain and a second peptide chain together having an overall sequence identity of at least 95% with the combined sequences of SEQ ID NO: 3 and SEQ ID NO: 4.

7. The method of claim 1, wherein the isolated heterodimeric protein has a first peptide chain and a second peptide chain together having an overall sequence identity of at least 98% with the combined sequences of SEQ ID NO: 3 and SEQ ID NO: 4.

8. The method of claim 5, wherein the single chain protein has an overall sequence identity of at least 95% with the combined amino acid sequences of SEQ ID NO: 3 and SEQ ID NO: 4.

9. The method of claim 5, wherein the single chain protein has an overall sequence identity of at least 98% with the combined amino acid sequences of SEQ ID NO: 3 and SEQ ID NO: 4.

10. The method of claim 1, wherein the isolated heterodimeric protein is immobilized to a solid or soluble support and/or has been provided with a detectable label.

11. The method of claim 5, wherein the single chain protein is immobilized to a solid or soluble support and/or has been provided with a detectable label.

12. A method according to claim 5, which comprises detecting the presence in the sample of IgE and/or IgG antibodies specifically binding to said single chain protein.

13. The method according to claim 5, further comprising the steps of
- contacting the immunoglobulin-containing body fluid sample from the patient suspected of having Type 1 allergy with at least one further purified allergen component from horse; and
- detecting the presence, in the sample, of IgE antibodies specifically binding to said purified allergen component from horse.

14. The method according to claim 13, wherein the further purified allergen component from horse is selected from the group consisting of native and recombinant Equ c 1, Equ c 2, Equ c 3, Equ c 4/5, and Equ c 15k.

* * * * *

SEQUENCE LISTING

```
<160> NUMBER OF SEQ ID NOS: 48

<210> SEQ ID NO 1
<211> LENGTH: 92
<212> TYPE: PRT
<213> ORGANISM: Equus caballus
<220> FEATURE:
<221> NAME/KEY: SIGNAL
<222> LOCATION: (1)..(22)
<220> FEATURE:
<221> NAME/KEY: mat_peptide
<222> LOCATION: (23)..(92)

<400> SEQUENCE: 1

Met Lys Arg Ala Gly Ala Leu Val Leu Leu Trp Thr Thr Leu Leu Leu
     -20                 -15                 -10
```

```
Ile Pro Gly Arg Asn Cys Asp Ile Cys Pro Ala Val Lys Glu Asp Val
        -5              -1   1               5                  10

Asn Ile Phe Leu Thr Gly Thr Pro Asp Asp Tyr Val Lys Val Ser
                    15              20              25

Gln Tyr Gln Arg Asn Pro Val Ile Leu Ala Asn Ala Glu Lys Leu Lys
            30                  35              40

Asn Cys Ile Asp Lys Lys Leu Thr Ala Glu Asp Lys Glu Asn Ala Leu
            45              50              55

Ser Val Leu Glu Lys Ile Tyr Ser Ser Asp Phe Cys
    60              65              70
```

<210> SEQ ID NO 2
<211> LENGTH: 114
<212> TYPE: PRT
<213> ORGANISM: Equus caballus
<220> FEATURE:
<221> NAME/KEY: SIGNAL
<222> LOCATION: (1)..(23)
<220> FEATURE:
<221> NAME/KEY: mat_peptide
<222> LOCATION: (24)..(114)

<400> SEQUENCE: 2

```
Met Lys Gly Ala Leu Leu Val Leu Ala Leu Val Thr Arg Glu Leu
            -20             -15             -10

Gly Ile Lys Met Ala Glu Ala Cys Pro Ser Phe Tyr Ala Val Leu Gly
        -5              -1   1               5

Val Leu Ser Leu Gly Ser Lys Thr Leu Leu Asp Thr Ser Leu Asn Leu
10              15              20              25

Val Asn Ala Thr Glu Pro Glu Lys Val Ala Met Gly Lys Ile Gln Asp
                30              35              40

Cys Tyr Asn Glu Ala Gly Val Ile Thr Lys Ile Ser Asp Leu Ile Ile
            45              50              55

Met Gly Thr Ile Thr Thr Ser Pro Glu Cys Ile Ser His Ala Leu Ser
            60              65              70

Thr Leu Thr Thr Asp Val Gln Glu Gly Ile Ser Lys Leu Asn Pro Leu
    75              80              85

Gly Arg
90
```

<210> SEQ ID NO 3
<211> LENGTH: 70
<212> TYPE: PRT
<213> ORGANISM: Equus caballus

<400> SEQUENCE: 3

```
Asp Ile Cys Pro Ala Val Lys Glu Asp Val Asn Ile Phe Leu Thr Gly
1               5                   10                  15

Thr Pro Asp Asp Tyr Val Lys Lys Val Ser Gln Tyr Gln Arg Asn Pro
            20                  25                  30

Val Ile Leu Ala Asn Ala Glu Lys Leu Lys Asn Cys Ile Asp Lys Lys
            35                  40                  45

Leu Thr Ala Glu Asp Lys Glu Asn Ala Leu Ser Val Leu Glu Lys Ile
    50                  55                  60

Tyr Ser Ser Asp Phe Cys
65                  70
```

<210> SEQ ID NO 4
<211> LENGTH: 91

```
<212> TYPE: PRT
<213> ORGANISM: Equus caballus

<400> SEQUENCE: 4

Cys Pro Ser Phe Tyr Ala Val Leu Gly Val Leu Ser Leu Gly Ser Lys
1               5                   10                  15

Thr Leu Leu Asp Thr Ser Leu Asn Leu Val Asn Ala Thr Glu Pro Glu
            20                  25                  30

Lys Val Ala Met Gly Lys Ile Gln Asp Cys Tyr Asn Glu Ala Gly Val
        35                  40                  45

Ile Thr Lys Ile Ser Asp Leu Ile Ile Met Gly Thr Ile Thr Thr Ser
    50                  55                  60

Pro Glu Cys Ile Ser His Ala Leu Ser Thr Leu Thr Thr Asp Val Gln
65                  70                  75                  80

Glu Gly Ile Ser Lys Leu Asn Pro Leu Gly Arg
                85                  90

<210> SEQ ID NO 5
<211> LENGTH: 185
<212> TYPE: PRT
<213> ORGANISM: Artificial Sequence
<220> FEATURE:
<223> OTHER INFORMATION: Synthetic single chain protein
<220> FEATURE:
<221> NAME/KEY: INIT_MET
<222> LOCATION: (1)..(1)
<220> FEATURE:
<221> NAME/KEY: MISC_FEATURE
<222> LOCATION: (72)..(86)
<223> OTHER INFORMATION: Linker peptide
<220> FEATURE:
<221> NAME/KEY: MISC_FEATURE
<222> LOCATION: (180)..(185)
<223> OTHER INFORMATION: Hexahistidine tag

<400> SEQUENCE: 5

Met Asp Ile Cys Pro Ala Val Lys Glu Asp Val Asn Ile Phe Leu Thr
1               5                   10                  15

Gly Thr Pro Asp Asp Tyr Val Lys Lys Val Ser Gln Tyr Gln Arg Asn
            20                  25                  30

Pro Val Ile Leu Ala Asn Ala Glu Lys Leu Lys Asn Cys Ile Asp Lys
        35                  40                  45

Lys Leu Thr Ala Glu Asp Lys Glu Asn Ala Leu Ser Val Leu Glu Lys
    50                  55                  60

Ile Tyr Ser Ser Asp Phe Cys Gly Gly Gly Ser Gly Gly Gly Gly
65                  70                  75                  80

Ser Gly Gly Gly Gly Ser Cys Pro Ser Phe Tyr Ala Val Leu Gly Val
                85                  90                  95

Leu Ser Leu Gly Ser Lys Thr Leu Leu Asp Thr Ser Leu Asn Leu Val
            100                 105                 110

Asn Ala Thr Glu Pro Glu Lys Val Ala Met Gly Lys Ile Gln Asp Cys
        115                 120                 125

Tyr Asn Glu Ala Gly Val Ile Thr Lys Ile Ser Asp Leu Ile Ile Met
    130                 135                 140

Gly Thr Ile Thr Thr Ser Pro Glu Cys Ile Ser His Ala Leu Ser Thr
145                 150                 155                 160

Leu Thr Thr Asp Val Gln Glu Gly Ile Ser Lys Leu Asn Pro Leu Gly
                165                 170                 175

Arg Leu Glu His His His His His
            180                 185
```

<210> SEQ ID NO 6
<211> LENGTH: 555
<212> TYPE: DNA
<213> ORGANISM: Artificial Sequence
<220> FEATURE:
<223> OTHER INFORMATION: DNA encoding synthetic single chain peptide

<400> SEQUENCE: 6

```
atggacattt gccctgcggt taaagaggac gtcaacattt ttctgaccgg taccccagat      60
gattacgtca aaaaagtgag ccagtaccag cgtaacccgg ttattctggc aaatgccgag     120
aaactgaaga attgtatcga caaaaagctg acggctgagg ataaggaaaa cgccctgtct     180
gtcttggaga agatttacag cagcgacttc tgtggtggcg gtggcagcgg tggtggtggt     240
tcgggcggtg gcggcagctg cccgtccttc tatgcggtgc tgggtgttct gagcttaggt     300
agcaagaccc tgttggacac gagcctgaat ttggtgaatg cgactgaacc ggagaaagtc     360
gcaatgggca gatccaaga ttgctataac gaagcgggcg ttatcaccaa gatcagcgat     420
ctgatcatta tgggtacgat cacgaccagc ccggaatgta tctctcacgc gctgtccacc     480
ctgaccaccg acgtgcaaga gggcattagc aaactgaacc cgctgggtcg cctcgagcac     540
caccaccacc accac                                                      555
```

<210> SEQ ID NO 7
<211> LENGTH: 185
<212> TYPE: PRT
<213> ORGANISM: Artificial Sequence
<220> FEATURE:
<223> OTHER INFORMATION: Synthetic single chain peptide
<220> FEATURE:
<221> NAME/KEY: INIT_MET
<222> LOCATION: (1)..(1)
<220> FEATURE:
<221> NAME/KEY: MISC_FEATURE
<222> LOCATION: (93)..(107)
<223> OTHER INFORMATION: Linker peptide
<220> FEATURE:
<221> NAME/KEY: MISC_FEATURE
<222> LOCATION: (180)..(185)
<223> OTHER INFORMATION: Hexahistidine tag

<400> SEQUENCE: 7

```
Met Cys Pro Ser Phe Tyr Ala Val Leu Gly Val Leu Ser Leu Gly Ser
  1               5                  10                  15

Lys Thr Leu Leu Asp Thr Ser Leu Asn Leu Val Asn Ala Thr Glu Pro
             20                  25                  30

Glu Lys Val Ala Met Gly Lys Ile Gln Asp Cys Tyr Asn Glu Ala Gly
         35                  40                  45

Val Ile Thr Lys Ile Ser Asp Leu Ile Ile Met Gly Thr Ile Thr Thr
     50                  55                  60

Ser Pro Glu Cys Ile Ser His Ala Leu Ser Thr Leu Thr Thr Asp Val
 65                  70                  75                  80

Gln Glu Gly Ile Ser Lys Leu Asn Pro Leu Gly Arg Gly Gly Gly Gly
                 85                  90                  95

Ser Gly Gly Gly Gly Ser Gly Gly Gly Ser Asp Ile Cys Pro Ala
            100                 105                 110

Val Lys Glu Asp Val Asn Ile Phe Leu Thr Gly Thr Pro Asp Asp Tyr
        115                 120                 125

Val Lys Lys Val Ser Gln Tyr Gln Arg Asn Pro Val Ile Leu Ala Asn
    130                 135                 140
```

```
Ala Glu Lys Leu Lys Asn Cys Ile Asp Lys Lys Leu Thr Ala Glu Asp
145                 150                 155                 160

Lys Glu Asn Ala Leu Ser Val Leu Glu Lys Ile Tyr Ser Ser Asp Phe
            165                 170                 175

Cys Leu Glu His His His His His His
        180                 185

<210> SEQ ID NO 8
<211> LENGTH: 555
<212> TYPE: DNA
<213> ORGANISM: Artificial Sequence
<220> FEATURE:
<223> OTHER INFORMATION: DNA encoding synthetic single chain peptide

<400> SEQUENCE: 8
atgtgcccgt cgttttatgc agtcctgggt gttctgtctt tgggttctaa aactttgctg      60
gacacgagcc tgaatctggt gaatgcaacg agcctgaaaa aggtcgcgat gggcaagatt     120
caggactgtt acaacgaagc gggcgttatt accaagatca gcgacctgat cattatgggc     180
acgatcacca cgagcccaga gtgcatcagc cacgctttgt ccaccctgac caccgatgtc     240
caagagggca ttagcaagct gaacccgctg ggtcgcggtg gtggcggtag cggtggtggt     300
ggctccggtg gcggtggcag cgatatttgt ccggcggtga agaagatgt caacatcttc      360 ctgaccggta ccccggatga ttatgtgaaa aagttagcc ataccagcg taatccggtt       420 atcctggcca atgccgagaa actgaagaac tgcatcgaca aaaagctgac cgcagaggac     480
aaagaaaacg cgctgagcgt gctggagaag atttacagca gcgacttctg tctcgagcac     540
caccaccacc accac                                                      555

<210> SEQ ID NO 9
<211> LENGTH: 210
<212> TYPE: DNA
<213> ORGANISM: Artificial Sequence
<220> FEATURE:
<223> OTHER INFORMATION: Codon optimized chain 1

<400> SEQUENCE: 9
gacatttgcc ctgcggttaa agaggacgtc aacattttc tgaccggtac cccagatgat       60
tacgtcaaaa agtgagcca gtaccagcgt aacccggtta ttctggcaaa tgccgagaaa     120
ctgaagaatt gtatcgacaa aaagctgacg gctgaggata ggaaaacgc cctgtctgtc     180 ttggagaaga tttacagcag cgacttctgt                                      210

<210> SEQ ID NO 10
<211> LENGTH: 273
<212> TYPE: DNA
<213> ORGANISM: Artificial Sequence
<220> FEATURE:
<223> OTHER INFORMATION: Codon optimized chain 2

<400> SEQUENCE: 10
tgcccgtcgt tttatgcagt cctgggtgtt ctgtctttgg gttctaaaac tttgctggac      60
acgagcctga atctggtgaa tgcaacggag cctgaaaagg tcgcgatggg caagattcag     120
gactgttaca cgaagcggg cgttattacc aagatcagcg acctgatcat tatgggcacg     180
atcaccacga gcccagagtg catcagccac gctttgtcca ccctgaccac cgatgtccaa     240
gagggcatta gcaagctgaa cccgctgggt cgc                                  273

<210> SEQ ID NO 11
```

```
<211> LENGTH: 20
<212> TYPE: DNA
<213> ORGANISM: Artificial Sequence
<220> FEATURE:
<223> OTHER INFORMATION: Forward primer for chain 1, PCR 1

<400> SEQUENCE: 11
ataaaagggc tgcagaattg                                                    20

<210> SEQ ID NO 12
<211> LENGTH: 20
<212> TYPE: DNA
<213> ORGANISM: Artificial Sequence
<220> FEATURE:
<223> OTHER INFORMATION: Forward primer for chain 2, PCR 1

<400> SEQUENCE: 12
gcagcagaaa ccctgccctg                                                    20

<210> SEQ ID NO 13
<211> LENGTH: 18
<212> TYPE: DNA
<213> ORGANISM: Artificial Sequence
<220> FEATURE:
<223> OTHER INFORMATION: Forward primer for chain 1

<400> SEQUENCE: 13
gtgagcacct gccacctg                                                      18

<210> SEQ ID NO 14
<211> LENGTH: 20
<212> TYPE: DNA
<213> ORGANISM: Artificial Sequence
<220> FEATURE:
<223> OTHER INFORMATION: Forward primer for chain 2

<400> SEQUENCE: 14
gaagagcatt ctagcagttg                                                    20

<210> SEQ ID NO 15
<211> LENGTH: 19
<212> TYPE: DNA
<213> ORGANISM: Artificial Sequence
<220> FEATURE:
<223> OTHER INFORMATION: Reverse primer for chain 1

<400> SEQUENCE: 15
gaatcttcta atcagacac                                                     19

<210> SEQ ID NO 16
<211> LENGTH: 19
<212> TYPE: DNA
<213> ORGANISM: Artificial Sequence
<220> FEATURE:
<223> OTHER INFORMATION: Reverse primer for chain 2

<400> SEQUENCE: 16
ggtagaggag acaggtgtc                                                     19

<210> SEQ ID NO 17
<211> LENGTH: 23
<212> TYPE: PRT
<213> ORGANISM: Equus caballus

<400> SEQUENCE: 17

Asp Ile Cys Pro Ala Val Lys Glu Asp Val Asn Ile Phe Leu Thr Gly
```

```
1               5                   10                  15

Thr Pro Asp Asp Tyr Val Lys
            20

<210> SEQ ID NO 18
<211> LENGTH: 16
<212> TYPE: PRT
<213> ORGANISM: Equus caballus

<400> SEQUENCE: 18

Glu Asp Val Asn Ile Phe Leu Thr Gly Thr Pro Asp Asp Tyr Val Lys
1               5                   10                  15

<210> SEQ ID NO 19
<211> LENGTH: 17
<212> TYPE: PRT
<213> ORGANISM: Equus caballus

<400> SEQUENCE: 19

Glu Asp Val Asn Ile Phe Leu Thr Gly Thr Pro Asp Asp Tyr Val Lys
1               5                   10                  15

Lys

<210> SEQ ID NO 20
<211> LENGTH: 7
<212> TYPE: PRT
<213> ORGANISM: Equus caballus

<400> SEQUENCE: 20

Lys Val Ser Gln Tyr Gln Arg
1               5

<210> SEQ ID NO 21
<211> LENGTH: 6
<212> TYPE: PRT
<213> ORGANISM: Equus caballus

<400> SEQUENCE: 21

Val Ser Gln Tyr Gln Arg
1               5

<210> SEQ ID NO 22
<211> LENGTH: 10
<212> TYPE: PRT
<213> ORGANISM: Equus caballus

<400> SEQUENCE: 22

Asn Pro Val Ile Leu Ala Asn Ala Glu Lys
1               5                   10

<210> SEQ ID NO 23
<211> LENGTH: 15
<212> TYPE: PRT
<213> ORGANISM: Equus caballus

<400> SEQUENCE: 23

Leu Thr Ala Glu Asp Lys Glu Asn Ala Leu Ser Val Leu Glu Lys
1               5                   10                  15

<210> SEQ ID NO 24
<211> LENGTH: 7
<212> TYPE: PRT
<213> ORGANISM: Equus caballus
```

```
<400> SEQUENCE: 24

Ile Tyr Ser Ser Asp Phe Cys
1               5

<210> SEQ ID NO 25
<211> LENGTH: 16
<212> TYPE: PRT
<213> ORGANISM: Equus caballus

<400> SEQUENCE: 25

Cys Pro Ser Phe Tyr Ala Val Leu Gly Val Leu Ser Leu Gly Ser Lys
1               5                   10                  15

<210> SEQ ID NO 26
<211> LENGTH: 13
<212> TYPE: PRT
<213> ORGANISM: Equus caballus

<400> SEQUENCE: 26

Ile Gln Asp Cys Tyr Asn Glu Ala Gly Val Ile Thr Lys
1               5                   10

<210> SEQ ID NO 27
<211> LENGTH: 23
<212> TYPE: PRT
<213> ORGANISM: Equus caballus

<400> SEQUENCE: 27

Asp Ile Cys Pro Ala Val Lys Glu Asp Val Asn Ile Phe Leu Thr Gly
1               5                   10                  15

Thr Pro Asp Asp Tyr Val Lys
            20

<210> SEQ ID NO 28
<211> LENGTH: 16
<212> TYPE: PRT
<213> ORGANISM: Equus caballus

<400> SEQUENCE: 28

Glu Asp Val Asn Ile Phe Leu Thr Gly Thr Pro Asp Asp Tyr Val Lys
1               5                   10                  15

<210> SEQ ID NO 29
<211> LENGTH: 17
<212> TYPE: PRT
<213> ORGANISM: Equus caballus

<400> SEQUENCE: 29

Glu Asp Val Asn Ile Phe Leu Thr Gly Thr Pro Asp Asp Tyr Val Lys
1               5                   10                  15

Lys

<210> SEQ ID NO 30
<211> LENGTH: 7
<212> TYPE: PRT
<213> ORGANISM: Equus caballus

<400> SEQUENCE: 30

Lys Val Ser Gln Tyr Gln Arg
1               5

<210> SEQ ID NO 31
<211> LENGTH: 10
```

```
<212> TYPE: PRT
<213> ORGANISM: Equus caballus

<400> SEQUENCE: 31

Asn Pro Val Ile Leu Ala Asn Ala Glu Lys
1               5                   10

<210> SEQ ID NO 32
<211> LENGTH: 15
<212> TYPE: PRT
<213> ORGANISM: Equus caballus

<400> SEQUENCE: 32

Leu Thr Ala Glu Asp Lys Glu Asn Ala Leu Ser Val Leu Glu Lys
1               5                   10                  15

<210> SEQ ID NO 33
<211> LENGTH: 13
<212> TYPE: PRT
<213> ORGANISM: Equus caballus

<400> SEQUENCE: 33

Ile Gln Asp Cys Tyr Asn Glu Ala Gly Val Ile Thr Lys
1               5                   10

<210> SEQ ID NO 34
<211> LENGTH: 7
<212> TYPE: PRT
<213> ORGANISM: Equus caballus

<400> SEQUENCE: 34

Asp Ile Cys Pro Ala Val Lys
1               5

<210> SEQ ID NO 35
<211> LENGTH: 16
<212> TYPE: PRT
<213> ORGANISM: Equus caballus

<400> SEQUENCE: 35

Glu Asp Val Asn Ile Phe Leu Thr Gly Thr Pro Asp Asp Tyr Val Lys
1               5                   10                  15

<210> SEQ ID NO 36
<211> LENGTH: 7
<212> TYPE: PRT
<213> ORGANISM: Equus caballus

<400> SEQUENCE: 36

Lys Val Ser Gln Tyr Gln Arg
1               5

<210> SEQ ID NO 37
<211> LENGTH: 6
<212> TYPE: PRT
<213> ORGANISM: Equus caballus

<400> SEQUENCE: 37

Val Ser Gln Tyr Gln Arg
1               5

<210> SEQ ID NO 38
<211> LENGTH: 10
<212> TYPE: PRT
<213> ORGANISM: Equus caballus
```

-continued

```
<400> SEQUENCE: 38

Asn Pro Val Ile Leu Ala Asn Ala Glu Lys
1               5                   10

<210> SEQ ID NO 39
<211> LENGTH: 15
<212> TYPE: PRT
<213> ORGANISM: Equus caballus

<400> SEQUENCE: 39

Leu Thr Ala Glu Asp Lys Glu Asn Ala Leu Ser Val Leu Glu Lys
1               5                   10                  15

<210> SEQ ID NO 40
<211> LENGTH: 7
<212> TYPE: PRT
<213> ORGANISM: Equus caballus

<400> SEQUENCE: 40

Ile Tyr Ser Ser Asp Phe Cys
1               5

<210> SEQ ID NO 41
<211> LENGTH: 13
<212> TYPE: PRT
<213> ORGANISM: Equus caballus

<400> SEQUENCE: 41

Ile Gln Asp Cys Tyr Asn Glu Ala Gly Val Ile Thr Lys
1               5                   10

<210> SEQ ID NO 42
<211> LENGTH: 16
<212> TYPE: PRT
<213> ORGANISM: Equus caballus

<400> SEQUENCE: 42

Cys Pro Ser Phe Tyr Ala Val Leu Gly Val Leu Ser Leu Gly Ser Lys
1               5                   10                  15

<210> SEQ ID NO 43
<211> LENGTH: 24
<212> TYPE: PRT
<213> ORGANISM: Equus caballus

<400> SEQUENCE: 43

Ile Ser Asp Leu Ile Ile Met Gly Thr Ile Thr Thr Ser Pro Glu Cys
1               5                   10                  15

Ile Ser His Ala Leu Ser Thr Leu
            20

<210> SEQ ID NO 44
<211> LENGTH: 7
<212> TYPE: PRT
<213> ORGANISM: Equus caballus
<220> FEATURE:
<221> NAME/KEY: UNSURE
<222> LOCATION: (1)..(1)
<223> OTHER INFORMATION: Asp or Cys
<220> FEATURE:
<221> NAME/KEY: UNSURE
<222> LOCATION: (2)..(2)
<223> OTHER INFORMATION: Pro, Ile or Cys
<220> FEATURE:
<221> NAME/KEY: UNSURE
```

```
<222> LOCATION: (3)..(3)
<223> OTHER INFORMATION: Ser, Arg, or Cys
<220> FEATURE:
<221> NAME/KEY: UNSURE
<222> LOCATION: (4)..(4)
<223> OTHER INFORMATION: Phe, Pro, or Cys
<220> FEATURE:
<221> NAME/KEY: UNSURE
<222> LOCATION: (5)..(5)
<223> OTHER INFORMATION: Tyr, Ala, or Cys
<220> FEATURE:
<221> NAME/KEY: UNSURE
<222> LOCATION: (6)..(6)
<223> OTHER INFORMATION: Ala, Val, or Cys
<220> FEATURE:
<221> NAME/KEY: UNSURE
<222> LOCATION: (7)..(7)
<223> OTHER INFORMATION: Val, or Cys

<400> SEQUENCE: 44

Xaa Xaa Xaa Xaa Xaa Xaa Xaa
1               5

<210> SEQ ID NO 45
<211> LENGTH: 279
<212> TYPE: DNA
<213> ORGANISM: Equus caballus

<400> SEQUENCE: 45
atgaagcggg ctggtgctct cgtgctgctc tggaccacct tgcttctgat cccaggcaga      60
aattgtgaca tttgcccagc cgtgaaggaa gatgttaata tattcctgac aggaacccct     120
gatgactatg ttaaaaaagt ttcacagtac caacgcaatc ctgtaatatt ggccaatgct     180
gaaaagctaa agaactgcat tgataagaaa ttgacagccg aggataagga gaatgccctc     240
agtgtgctgg agaaaatata ctcaagtgat ttttgttaa                            279

<210> SEQ ID NO 46
<211> LENGTH: 345
<212> TYPE: DNA
<213> ORGANISM: Equus caballus

<400> SEQUENCE: 46
atgaaggggg cactgcttgt gctggccttg ctggtgacca gagagctggg catcaagatg      60
gcggaagctt gcccgagttt ttatgcagtc cttggtgtgt tgtcccttgg aagcaagaca     120
ctgttggaca cctccctcaa tctggtcaat gctactgaac cggaaaaagt agccatggga     180
aaaatccagg attgctacaa tgaggcggga gtcataacca agatctcgga tctgatcatc     240
atgggtacta tcaccaccag cccagaatgc atcagccacg cactgagcac attgacgacg     300
gatgttcaag aaggcatttc taagctgaac cctctgggga gatga                     345

<210> SEQ ID NO 47
<211> LENGTH: 88
<212> TYPE: PRT
<213> ORGANISM: Felis catus
<220> FEATURE:
<221> NAME/KEY: SIGNAL
<222> LOCATION: (1)..(18)

<400> SEQUENCE: 47

Met Leu Asp Ala Ala Leu Pro Pro Cys Pro Thr Val Ala Ala Thr Ala
1               5                   10                  15

Asp Cys Glu Ile Cys Pro Ala Val Lys Arg Asp Val Asp Leu Phe Leu
            20                  25                  30
```

-continued

```
Thr Gly Thr Pro Asp Glu Tyr Val Glu Gln Val Ala Gln Tyr Lys Ala
         35                  40                  45

Leu Pro Val Val Leu Glu Asn Ala Arg Ile Leu Lys Asn Cys Val Asp
         50                  55                  60

Ala Lys Met Thr Glu Glu Asp Lys Glu Asn Ala Leu Ser Leu Leu Asp
65                   70                  75                  80

Lys Ile Tyr Thr Ser Pro Leu Cys
                 85

<210> SEQ ID NO 48
<211> LENGTH: 109
<212> TYPE: PRT
<213> ORGANISM: Felis catus
<220> FEATURE:
<221> NAME/KEY: SIGNAL
<222> LOCATION: (1)..(23)

<400> SEQUENCE: 48

Met Arg Gly Ala Leu Leu Val Leu Ala Leu Leu Val Thr Gln Ala Leu
1               5                   10                  15

Gly Val Lys Met Ala Glu Thr Cys Pro Ile Phe Tyr Asp Val Phe Phe
                20                  25                  30

Ala Val Ala Asn Gly Asn Glu Leu Leu Leu Asp Leu Ser Leu Thr Lys
             35                  40                  45

Val Asn Ala Thr Glu Pro Glu Arg Thr Ala Met Lys Lys Ile Gln Asp
         50                  55                  60

Cys Tyr Val Glu Asn Gly Leu Ile Ser Arg Val Leu Asp Gly Leu Val
65                   70                  75                  80

Met Thr Thr Ile Ser Ser Ser Lys Asp Cys Met Gly Glu Ala Val Gln
                 85                  90                  95

Asn Thr Val Glu Asp Leu Lys Leu Asn Thr Leu Gly Arg
                 100                 105
```

UNITED STATES PATENT AND TRADEMARK OFFICE
CERTIFICATE OF CORRECTION

Page 1 of 1

PATENT NO. : 10,753,946 B2
APPLICATION NO. : 15/327253
DATED : August 25, 2020
INVENTOR(S) : Lars Mattsson et al.

It is certified that error appears in the above-identified patent and that said Letters Patent is hereby corrected as shown below:

On the Title Page

Item (30), change "1450907" to --1450907-9--.

Signed and Sealed this
Sixth Day of October, 2020

Andrei Iancu
*Director of the United States Patent and Trademark Office*